US008097728B2

(12) United States Patent  
Gu et al.

(10) Patent No.: US 8,097,728 B2
(45) Date of Patent: Jan. 17, 2012

(54) IMINOSUGAR COMPOUNDS WITH ANTIFLAVIRUS ACTIVITY

(75) Inventors: Baohua Gu, Malvern, PA (US); Timothy M. Block, Doylestown, PA (US); Robert M. Moriarty, Michigan City, IN (US); Mahendra N. Deshpande, Gurnee, IL (US); Rajendra C. Shah, Morton Grove, IL (US)

(73) Assignees: Philadelphia Health & Education Corporation, Philadelphia, PA (US); The Board Of Trustees Of The University of Illinois, Urbana, IL (US)

( * ) Notice: Subject to any disclaimer, the term of this patent is extended or adjusted under 35 U.S.C. 154(b) by 872 days.

(21) Appl. No.: 12/112,694

(22) Filed: Apr. 30, 2008

(65) Prior Publication Data

US 2009/0042268 A1 Feb. 12, 2009

Related U.S. Application Data

(60) Provisional application No. 60/914,889, filed on Apr. 30, 2007.

(51) Int. Cl.
C12N 9/99 (2006.01)
A61P 31/14 (2006.01)
C07D 211/40 (2006.01)

(52) U.S. Cl. ........................ 546/219; 435/184
(58) Field of Classification Search .................. None
See application file for complete search history.

(56) References Cited

U.S. PATENT DOCUMENTS

| 4,065,562 | A | 12/1977 | Ohata et al. |
| 4,182,767 | A | 1/1980 | Murai et al. |
| 4,246,345 | A | 1/1981 | Kinast et al. |
| 4,260,622 | A | 4/1981 | Junge et al. |
| 4,266,025 | A | 5/1981 | Kinast et al. |
| 4,405,714 | A | 9/1983 | Kinast et al. |
| 4,533,668 | A | 8/1985 | Matsumura et al. |
| 4,611,058 | A | 9/1986 | Koebernick |
| 4,639,436 | A | 1/1987 | Junge et al. |
| 4,806,650 | A | 2/1989 | Schröder et al. |
| 4,849,430 | A | 7/1989 | Fleet et al. |
| 4,957,926 | A | 9/1990 | Jacob et al. |
| 5,003,072 | A | 3/1991 | Partis et al. |
| 5,011,829 | A | 4/1991 | Hirsch et al. |
| 5,030,638 | A | 7/1991 | Partis et al. |
| 5,103,008 | A | 4/1992 | Scudder et al. |
| 5,144,037 | A | 9/1992 | Partis et al. |
| 5,151,519 | A | 9/1992 | Behling et al. |
| 5,401,645 | A | 3/1995 | Grabner et al. |
| 5,411,970 | A | 5/1995 | Partis et al. |
| 5,451,679 | A | 9/1995 | Barta et al. |
| 5,595,981 | A | 1/1997 | Barta et al. |
| 5,622,972 | A | 4/1997 | Bryant et al. |
| 6,225,325 | B1 | 5/2001 | Jacob |
| 6,465,487 | B1 | 10/2002 | Block et al. |
| 6,465,488 | B1 | 10/2002 | Butters et al. |
| 6,545,021 | B1 | 4/2003 | Mueller et al. |
| 6,610,703 | B1 | 8/2003 | Jacob et al. |
| 6,689,759 | B1 | 2/2004 | Jacob et al. |
| 6,809,083 | B1 | 10/2004 | Mueller et al. |
| 6,927,294 | B1 | 8/2005 | Petasis et al. |
| 2005/0058987 | A1 | 3/2005 | Shi et al. |
| 2005/0119310 | A1* | 6/2005 | Mueller et al. ............. 514/328 |
| 2006/0074107 | A1 | 4/2006 | Butters et al. |

FOREIGN PATENT DOCUMENTS

| WO | WO 87/03903 A1 | 7/1987 |
| WO | WO 95/19172 A1 | 7/1995 |
| WO | WO 99/29321 A1 | 6/1999 |
| WO | WO 2001/10429 A2 | 2/2001 |
| WO | WO 2006/061585 A1 | 6/2006 |

OTHER PUBLICATIONS

Vippagunta et al., Crystalline solids, 48 Adv. Drug Delivery Rev. 3-26 (2001).*
Dhavale et al., N-Hydroxyethyl-piperidine and -Pyrrolidine Homazasugars: Preparation and Evaluation of Glycosidase Inhibitory Activity, 11 Bioorg. & Med. Chem. 3295-3305 (2003).* Ramesh et al., Synthesis of Hydroxylated Cyclohexenyl- and Cyclohexanyladenines as Potential Inhibitors of S-Adenosylhomocysteine Hydrolase, 57 J. Org. Chem. 5861-5868 (1992).*
An, J. et al., "Development of a novel mouse model for dengue virus infection," Virology, 1999, 263(1), 70-77.
Beasley, D.W.C. et al., "West Nile Virus Strains Differ in Mouse Neurovirulence and Binding to Mouse or Human Brain Membrane Receptor Preparations," Dec. 2001, Annals of the New York Academy of Sciences, vol. 951, pp. 332-335.

(Continued)

Primary Examiner — Janet Andres
Assistant Examiner — Timothy R Rozof
(74) Attorney, Agent, or Firm — Woodcock Washburn, LLP

(57) ABSTRACT

An anti-viral compounds effective against viruses belonging to the Flaviviridae family, wherein the anti-viral compounds are 1,5-dideoxy-1,5-imino-D-glucitol derivative compounds having the general formula (I)

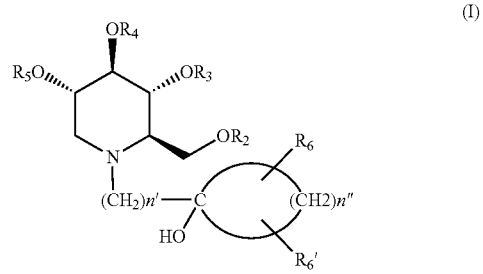

(I)

wherein $R^2$, $R^3$, $R^4$ and $R^5$ are the same or different and are selected from the group consisting of hydrogen, acyl, benzyl, alkyl, aryl, sulfonyl, phosphonyl, silyl, $R_6$ is at least one of alkyl or branched alkyl, heteroalkyl or aryl, $R_6'$ is a bridging group selected from at least one of bicycle[2.2.1]heptyl, bicycle[3.2.1]octyl, oxa analogs, admonyl and cubyl, n'=2-10, n"=1-10, enantiomers and stereoisomers of said compounds and physiologically acceptable salts or solvates of said compounds, enantiomer or stereoisomer.

20 Claims, 7 Drawing Sheets

OTHER PUBLICATIONS

Bergeron JJ, Brenner MB, Thomas DY, and Williams DB (1994). "Calnexin: a membrane-bound chaperone of the endoplasmic reticulum" Trends Biochem Sci 19: 124-8.

Block TM, and Jordan R (2001). "Iminosugars as possible broad spectrum anti hepatitis virus agents: the glucovirs and alkovirs," Antivir Chem Chemother 12: 317-25.

Block TM, Lu X, Platt FM, Foster GR, Gerlich WH, Blumberg BS, and Dwek RA (1994). "Secretion of human hepatitis B virus is inhibited by the imino sugar N-butyldeoxynojirimycin" Proc Natl Acad Sci U S A 91: 2235-9.

Blum, H. E. et al., "Antiviral therapy of hepatitis B virus infection: Blocking viral gene expression," Advanced Drug Delivery Reviews, 1995, 17, 321-331.

Brinton, M.A. et al., "Sequence and Secondary Structure Analysis of the 5'-Terminal Region of Flavivirus Genome RNA," Virology, 1988, 162, 290-299.

Bryant, M. et al., 10th International Conference of AIDS, Berlin, Jun. 7-11, 1993, Abstr. No. WS-A11-2.

Campbell, M. S. et al., "Infectious cDNA Clones of Langat Tick-Borne Flavivirus That Differ from Their Parent in Peripheral Neurovirulence," Virol., 2000, 269, 225-237.

Chambers, T.J. et al., "Flavivirus genome organization, expression, and replication," Ann Rev. Microbiol., 1990, 44, 649-688.

Chapel C, Garcia C, Roingeard P, Zitzmann N, Dubuisson J, Dwek RA, Trepo C, Zoulim F, and Durantel D (2006). "Antiviral effect of alpha-glucosidase inhibitors on viral morphogenesis and binding properties of hepatitis C virus-like particles" J Gen Virol 87: 861-71.

Chapman, T. M. et al., "Glyco- and peptidomimetics from three-component Joullie-Ugi coupling show selective antiviral activity," J. Am Chem. Soc., 2005, 127(2), 506-507.

Coates, J.A.V. et al., "Developments in viral hepatitis during 1994," Exp. Opin. Ther. Patents, 1995, 5(8), 747-756.

Durantel D, Branza-Nichita N, Carrouee-Durantel S, Butters TD, Dwek RA, and Zitzmann N (2001). "Study of the mechanism of antiviral action of iminosugar derivatives against bovine viral diarrhea virus," J Virol 75: 8987-98.

Elbein, A.D., "Inhibitors of the Biosynthesis and processing of N-linked oligosaccharide chains," Ann. Rev. Biochem., 1987, 56, 497-534.

Ellgaard L, Molinari M, and Helenius A (1999). "Setting the standards: quality control in the secretory pathway," Science 286: 1882-8.

Ganem, B., "N-Butyldeoxynojirimycin is a Novel Inhibitor of Glycolipid Biosynthesis. Secretion of Human Hepatitis B Virus Is Inhibited by the Imino Sugar N-Butyldeoxynojirimycin," Chemtracts: Organic Chemistry, 1994, 7(2), 106-107.

Gentry M K, Henchal EA, McCown JM, Brandt WE, and Dalrymple JM (1982). "Identification of distinct antigenic determinants on dengue-2 virus using monoclonal antibodies," Am J Trop Med Hyg 31: 548-55.

Gu B, Liu C, Lin-Goerke J, Maley DR, Gutshall LL, Feltenberger CA, and Del Vecchio AM (2000). "The RNA helicase and nucleotide triphosphatase activities of the bovine viral diarrhea virus NS3 protein are essential for viral replication," J Virol 74: 1794-800.

Gu B, Ouzunov S, Wang L, Mason P, Bourne N, Cuconati A, and Block TM (2006). "Discovery of small molecule inhibitors of West Nile virus using a high-throughput sub-genomic replicon screen," Antiviral Res 70:39-50.

Gubler, D. J., "Dengue and Dengue Hemorrhagic Fever," Clin. Microb. Revs., 1998, 11(3), 480-496.

Guo, J. T. et al., "West Nile Virus inhibits the signal transduction pathway of alpha interferon," J. Virology, 2005, 79(3), 1343-1350.

Helenius A, and Aebi M (2004). "Roles of N-linked glycans in the endoplasmic reticulum," Annu Rev Biochem 73: 1019-49.

Hollinger, F. B., in Fields Virology, Third Ed., vol. 2, 1996, Bernard N. Fields et al., Eds., Chapter 86, "Hepatitis B Virus,", pp. 2738-2807, Lippincott-Raven, Philadelphia, PA.

Hoofnagle, J.H. et al., "The treatment of chronic viral hepatitis," 1997, New Engl. J. Med., 336(5), 347-356.

Hurrelbrink, R. J. et al., "Characterization of infectious Murray Valley encephalitis virus derived from a stably cloned genome-length cDNA," J. Gen. Virol., 1999, 80, 3115-3125.

Jordan R, Nikolaeva OV, Wang L, Conyers B, Mehta A, Dwek RA, and Block TM (2002). "Inhibition of host ER glucosidase activity prevents Golgi processing of virion-associated bovine viral diarrhea virus E2 glycoproteins and reduces infectivity of secreted virions," Virology 295:10-9.

Jordan, I. et la., "Ribavirin Inhibits West Nile Virus Replication and Cytopathic Effect in Neural Cells," J. Infect Dis., 2000, 182, 1214-1217.

Kapoor, M. et al., "Synthesis and characterization of an infectious dengue virus type-2 RNA genome (New Guinea C strain)," Gene, 1995, 162, 175-180.

Khromykh, A. A. et al., "Completion of Kunjin Virus RNA Sequence and Recovery of an Infectious RNA Transcribed from Stably Cloned Full-Length cDNA," J. Virol., 1994, 68(7), 4580-4588.

Khromykh, A. A. et al., "Subgenomic Replications of the Flavivirus Kunjin: Construction and Applications," J. Virol., 1997, 71(2), 1497-1505.

Lai, C. J. et al., "Infectious RNA transcribed from stably cloned full-length cDNA of dengue type 4 virus," Proc. Natl. Acad. Sci. U.S.A., 1991, 88, 5139-5143.

Lanciotti, R. et al., "Origin of the West Nile Virus Responsible for an Outbreak of Encephalitis in the Northeastern United States," Science, 1999, 286, 2333-2337.

Lanciotti, R. et al., "Complete Genome Sequences and Phylogenetic Analysis of West Nile Virus Strains Isolated from the United States, Europe, and the Middle East," Virology, 2002, 298, 96-105.

Lindenbach, B.D. et al. (2001) "Flaviviridae: The Viruses and their Replication," in Fields Virology, D.M. Knipe and P.M. Howley (eds.), 4th ed., Ch. 32, vol. 1, Lippincott Williams & Wilkins, Philadelphia, PA, pp. 991-1041.

Locarnini, S. A. et al., "Hepatitis B: New approaches for antiviral chemotherapy," Antiviral Chemistry & Chemotherapy, 1996, 7(2), 53-64.

Mackenzie JM, and Westaway EG (2001). "Assembly and maturation of the flavivirus Kunjin virus appear to occur in the rough endoplasmic reticulum and along the secretory pathway, respectively," J Virol 75: 10787-99.

Mandl, C. W. et al., "Infectious cDNA clones of tick-borne encephalitis virus European subtype prototypic strain Neudoerfl and high virulence strain Hypr," J. Gen. Virol., 1997, 78, 1049-1057.

Mehta A, Carrouee S, Conyers B, Jordan R, Butters T, Dwek R A, and Block TM (2001). "Inhibition of hepatitis B virus DNA replication by imino sugars without the inhibition of the DNA polymerase: therapeutic implications," Hepatology 33: 1488-95.

Mehta A, Conyers B, Tyrrell DL, Walters KA, Tipples GA, Dwek RA, and Block TM (2002). "Structure-activity relationship of a new class of anti-hepatitis B virus agents," Antimicrob Agents Chemother 46: 4004-8.

Mehta A, Lu X, Block TM, Blumberg BS, and Dwek RA (1997). "Hepatitis B virus (HBV) envelope glycoproteins vary drastically in their sensitivity to glycan processing: evidence that alteration of a single N-linked glycosylation site can regulate HBV secretion," Proc Natl Acad Sci U S A 94: 1822-7.

Mehta A, Ouzounov S, Jordan R, Simsek E, Lu X, Moriarty RM, Jacob G, Dwek RA, and Block TM (2002b). "Imino sugars that are less toxic but more potent as antivirals, in vitro, compared with N-n-nonyl DNJ," Antivir Chem Chemother 13: 299-304.

Mehta AS, Gu B, Conyers B, Ouzounov S, Wang L, Moriarty RM, Dwek RA, and Block TM (2004). "alpha-Galactosylceramide and novel synthetic glycolipids directly induce the innate host defense pathway and have direct activity against hepatitis B and C viruses," Antimicrob Agents Chemother 48:2085-90.

Monath, T. J. et al., "A Live attenuated recombinant West Nile Virus Vaccine," Proc. Natl. Acad. Sci. USA, 2006, 103, 6694-6699.

Morrey, J. D. et al., "Identification of active antiviral compounds against a New York isolate of West Nile virus," Antiviral Res., 2002, 55, 107-116.

Newbrun, E. et al., "Inhibition by Acarbose, Nojirimycin and 1-Deoxynojirimycin of Glucosyltransferase produced by oral *Streptococci*," Arch. Oral Biol., 1983, 28(6), 516-536.

Norton PA, Conyers B, Gong Q, Steel LF, Block TM, and Mehta AS (2005). "Assays for glucosidase inhibitors with potential antiviral activities: secreted alkaline phosphatase as a surrogate marker," J Virol Methods 124:167-72.

Ou WJ, Cameron PH, Thomas DY, and Bergeron JJ (1993). "Association of folding intermediates of glycoproteins with calnexin during protein maturation," Nature 364:771-6.

Ouzounov S, Mehta A, Dwek RA, Block TM, and Jordan R (2002). "The combination of interferon alpha-2b and n-butyl deoxynojirimycin has a greater than additive antiviral effect upon production of infectious bovine viral diarrhea virus (BVDV) in vitro: implications for hepatitis C virus (HCV) therapy," Antiviral Res :425-35.

Polo, S. et al., "Infectious RNA Transcripts from Full-Length Dengue Virus Type 2 cDNA Clones Made in Yeast," J. Virol, 1997, 71(7), 5366-5374.

Proutski, V. et al., "Secondary structure of the 3' untranslated region of flaviviruses: similarities and differences," Nucleic Acids, 1997, 25(6), 1194-1202.

Rauscher, S. et al., "Secondary structure of the 3'-noncoding region of flavivirus genomes: Comparative analysis of base pairing probabilities," RNA, 1997, 3, 779-791.

Rice, C. M. et al., "Nucleotide Sequence of Yellow Fever Virus: Implications for Flavivirus Gene Expression and Evolution," Science, 1985, 229, 726-733.

Rossi SL, Zhao Q, O'Donnell VK, and Mason PW (2005). "Adaptation of West Nile virus replicons to cells in culture and use of replicon-bearing cells to probe antiviral action," Virology 331:457-70.

Saunier, B. et al., "Inhibition of N-linked Complex Oligosaccharide Formulation by 1-Deoxynojirimycin, an Inhibitor of Processing Glucosidases," J. Biol. Chem., 1982, 257, 14155-14161.

Sells MA, Chen ML, and Acs G (1987). "Production of hepatitis B virus particles in Hep G2 cells transfected with cloned hepatitis B virus DNA," Proc Natl Acad Sci U S A 84:1005-9.

Simon, D.M. et al., "Treatment of Chronic Hepatitis C with Interferon Alfa-n3: A Multicenter, Randomized, Open-Label Trial," Hepatology, 1997, 25, 445-448.

Simsek E, Mehta A, Zhou T, Dwek RA, and Block TM (2005). "Hepatitis B virus large and middle glycoproteins are degraded by a proteasome pathway in glucosidase-inhibited cells but not in cells with functional glucosidase enzyme," J Virol 79:, 12914-20.

Solomon, T. R. et al., "Poliomyelitis like illness due to Japanese encephalitis virus," Lancet, 1998, 351, 1094-1097.

Sumiyoshi, H. et al., "Infectious Japanese Encephalitis Virus RNA can Be synthesized form In Vitro-Ligated cDNA Templates," J. Virol., 1992, 66(9), 5425-5431.

Tan A, van den Broek L, Bolscher J, Vermaas DJ, Pastoors L, van Boeckel C, and Ploegh H (1994). "Introduction of oxygen into the alkyl chain of N-decyl-dNM decreases lipophilicity and results in increased retention of glucose residues on N-linked oligosaccharides," Glycobiology 4:141-9.

Tan A, van den Broek L, van Boeckel S, Ploegh H, and Bolscher J (1991). "Chemical modification of the glucosidase inhibitor 1-deoxynojirimycin. Structure-activity relationships,". J Biol Chem 266:14504-10.

Tomori, O., "Impact of yellow fever virus on the developing world," Adv. Virus Res., 1999, 53, 5-34.

van den Broek et al., "Synthesis of oxygen-substituted N-alkyl 1-deoxynojirimycin derivatives: aza sugar α-glucosidase inhibitors showing antiviral (HIV-1) and immunosuppressive activity," 1994, Recl. Trav. Chim. Pays-Bas, 113(11), 507-516.

Wang, Y-F. et al., "Chemo-enzymatic Synthesis of Five-membered Azasugars as Inhibitors of Fucosidase and Fucosyltransferase: An Issue Regarding the Stereochemistry Discrimination at Transition States," Tetrahedron Lett, 1993, 34(3), 403-406.

Wu SF, Lee CJ, Liao CL, Dwek RA, Zitzmann N, and Lin YL (2002). "Antiviral effects of an iminosugar derivative on flavivirus infections,". J Virol 76:3596-604.

Yamshchikov, V. F. et al., "An Infectious Clone of the West Nile Flavivirus," Virology, 2001, 281, 294-304.

Zitzmann N, Mehta AS, Carrouee S, Butters TD, Platt FM, McCauley J, Blumberg B. S., Dwek RA, and Block TM (1999). "Imino sugars inhibit the formation and secretion of bovine viral diarrhea virus, a pestivirus model of hepatitis C virus: implications for the development of broad spectrum anti-hepatitis virus agents," Proc Natl Acad Sci U S A 96:11878-82.

\* cited by examiner

A

A

B

IMINOSUGAR COMPOUNDS WITH ANTIFLAVIRUS ACTIVITY

CROSS-REFERENCE TO RELATED APPLICATIONS

This application claims benefit to U.S. Provisional Application No. 60/914,889, filed Apr. 30, 2007, the entire contents of each of which are incorporated by reference herein, in their entirety.

GOVERNMENT SUPPORT

This research was supported in part by U.S. Government funds (National Institutes of Health grant numbers UO1 AI54764-02, U01 AI061441-02 and U01 AI61441-01) and the U.S. Government may therefore have certain rights to aspects of the invention.

FIELD OF THE INVENTION

This invention relates to the field of antiviral compounds and compositions for the treatment against flaviviral infections. More specifically, it relates to novel flavivirus replication inhibitors, bis-amide pyrolidine derivatives, and pharmaceutical compositions and the use thereof to treat disorders caused by West Nile virus, Bovine Viral Diarrhea virus, Hepatitis B virus and other emerging flaviviruses, such as, for example, JEV, SLEV, AV, KV, JV, CV, YV, TBEV, dengue viruses (e.g., DENV-1, DENV-2, DENV-3, DENV-4), YFV and MVEV.

BACKGROUND OF THE INVENTION

West Nile virus (WNV) is a mosquito-borne virus that has been introduced to the U.S. in 1999 (Solomon et al, 1998; Gubler, 1998 Monath, 2005, Tomorri, 1999). Since the initial outbreak, there have been cases reported in all but two states in the U.S. WNV has increasingly become a public health threat, causing hundreds of deaths and tens of thousands of infections (Solomon et al, 1998; Gubler, 1998 Monath, 2005, Tomorri, 1999). Although there has been progress in vaccine development to prevent WNV encephalitis in humans (Rossi 2005), there is still no effective vaccine or antiviral drug therapy (Rossi 2005). Currently, the only available treatment is supportive, and the only existing means of prevention is mosquito control, which is also of limited success. It is also considered to be an agent of bioterrorism concern (Monath 2005), and therefore, safe and effective antiviral drugs to treat WNV infection are urgently needed.

WNV is a positive, single stranded RNA virus (Rossi 2005). It belongs to the Flaviviridae family, and Flavivirus genus. Many flaviviruses are significant human pathogens. In addition to WNV, this flavivirus sero-complex includes Japanese encephalitis virus (JEV), St. Louis encephalitis (SLEV), Alfuy virus (AV), Koutango virus (KV), Kunjin virus (JV), Cacipacore virus (CV), Yaounde virus (YV), and Murray Valley encephalitis virus (MVEV). The Flaviviridae family also includes the Tick-borne encephalitis virus (TBEV), Dengue virus (including the four serotypes of: DENV-1, DENV-2, DENV-3, and DENV-4), and the family prototype, Yellow Fever virus (YFV).

Flaviviruses are the most significant group of arthropod-transmitted viruses in terms of global morbidity and mortality. A combined toll of hundreds of millions of infections around the world annually coupled with the lack of sustained mosquito control measures, has distributed flaviviruses throughout the tropics, subtropics, and temperate areas. As a result, over half the world's population is at risk for flaviviral infection. Further, modern jet travel and human migration have raised the potential for global spread of these pathogens. Strains of WNV are categorized into two different phylogenetic lineages, namely, lineage I and II, which share 75% nucleotide sequence identity (Lanciotti, R et al, (2002) Virology 298:96-105). Lineage I strains have been isolated from human and equine epidemic outbreaks from around the world and constitute the main form of human pathogen. Sequence analysis indicates that the current epidemic strain in North America belongs to lineage I. Lineage II strains are rarely isolated from humans and are geographically restricted primarily to sub-Saharan Africa and Madagascar. The differences in disease patterns of lineage I and II strains are postulated to be the result of differences in vector competence (host compatibility), virulence, and transmission cycles of the strains, as well as, host immunity (Beasley, D. W. C. et al, (2001) International Conference on the West Nile Virus, New York Academy of Science Poster Section 1:5). Sequence analysis showed that the strain in North America is closely related to other human epidemic strains isolated from Israel, Romania, Russia, and France, all of which belong to lineage I (Lanciotti, R. et al. (1999) Science 286:2333-2337).

The flavivirus genome, including the genome of WNV, is a single positive-sense RNA of approximately 10,500 nucleotides containing short 5' and 3' untranslated regions (UTR), a single long open reading frame (ORF), a 5' cap region, and a non-polyadenylated 3' terminus. The entire genome is transcribed as a single polycistronic messenger RNA molecule, which is then translated as a polyprotein. Individual proteins are subsequently produced by proteolytic processing of the polyprotein, which is directed by viral and host cell proteases (Chambers, T. J. et al, (1990) Ann. Rev. Microbiol. 44: 649-688; Lindenbach, B. D. and C. M. Rice, (2001) In D. M. Knipe and P. M. Howley (ed), Fields virology, 4.sup.th ed., vol. 1. Lippincott Williams & Wilkins, Philadelphia, Pa.).

During the replication cycle of flaviviruses, especially WNV, synthesis of positive and negative (hereafter referred to as plus (+) and minus (−), respectively) sense RNAs is asymmetric. In the case of WNV, plus-sense RNAs are produced in 10- to 100-fold excess over minus-sense RNA. Regulatory sequences in the 3' UTR are believed to function as a promoter for initiation of minus-strand RNA synthesis. Deletion of this region ablates viral infectivity (Brinton, M. A. et al, (1986) Virology 162: 290-299; Proutski, V., et al (1997) Nucleic Acids Res. 25: 1194-1202; Rauscher, S., et al (1997) RNA 3: 779-791).

WVN genome is 12 kilobases in length and has a 5' and 3' non-translated region (NTR). The coding sequences specify a single polyprotein, which is proteolytically processed into approximately a dozen functional proteins by both viral and cellular proteases (5). The genes for structural proteins, namely capsid (C), membrane (M; which exists in cells as its precursor, prM), and envelope (E) are located in the 5' region of the genome, where those for the nonstructural proteins (NS), namely, NS1, NS2A, NS2B, NS3, NS4A, NS4B, and NS5 (5) are located at the 3' portion of the genome. WNV can infect many cell types and produce cytopathic plaques. However, due to the highly infectious nature, infections must be carried out in BL3 labs, limiting the use of the plaque assay to screen large number of compounds.

The development of therapeutic drugs and/or vaccines to treat and/or immunize against WNV and other flavivirus infections is urgently needed and of great importance to global public health. To achieve this goal, high-throughput screening assays were developed to facilitate the identification of novel chemotherapeutics effective against flaviviruses or vaccines capable of establishing a protective immune response to flaviviruses (see U.S. Patent Application Publication No. 2005/0058987 to Shi et al.). Two general strategies to be adapted for the screening and identification of novel chemotherapeutic antiflaviviral compounds and/or vaccines are based on biochemical and genetic approaches.

Assays for screening antiviral compounds that are based on biochemical approaches typically involve testing compounds for activities that limit or inhibit viral enzymes or proteins that are essential for viral propagation. For example, NS3, which has protease, helicase and NTPase activity, and NS5, which has an RNA-dependent RNA polymerase and methyltransferase activity, are key components of viral replication complex and thus, are ideal targets for antiviral screening. Further, three-dimensional structures of viral proteins, if available, can afford the possibility for rational design of drugs that will inhibit their activity, i.e., designing drugs based on the knowledge of the structure and shape of the active sites of the protein. For example, the crystal structures of the DENV NS3 protease domain and NS5 cap methyltransferase fragment have been solved and thus, the possibility of rationally designing small molecules to inhibit the active sites of NS3 and NS5 is feasible. Although biochemical approaches are capable of identifying potential viral inhibitors, they are limited in their overall efficiency since only a single enzyme or protein can be tested for any potential assay. Thus, individual assays would be required to screen for inhibitors of each given viral target protein.

In contrast, assays utilizing a genetic approach, which are usually cell-based, offer a number of advantages over biochemical approaches. One major advantage of a genetic approach based assay is that multiple viral protein targets can be analyzed simultaneously. A second major advantage is that, since genetic assays involve the use of living cells and the uptake of compounds therein, the screening assay is administered in a more authentic therapeutic environment. Accordingly, inhibitors identified through cell-based assays typically have a higher success rate in subsequent animal experiments.

A cell-based assay available for screening for flaviviral inhibitors involves the infection of cultured cells with virus and the subsequent monitoring for potential inhibition in the presence of a potential inhibitor through observation or quantification of cytopathic effects (J. D. Morrey et al., Antiviral Res (2002) 55:107-116; I. Jordan, J. Infect. Dis. (2000) 182: 1214-1217) or quantification of viral RNA by reverse transcriptase (RT)-PCR(S. F. Wu, J. Virol. (2002) 76:3596-3604). These assays are highly labor-intensive and impossible to use when screening compound libraries in large quantities.

Genetic high-throughput cell-based screening assays for the rapid screening and identification of potential inhibitors from compound libraries utilizing cDNA clones of RNA viruses are preferred screening tools for identifying potential inhibitors.

For example, two kinds of reverse genetics systems, full-length infectious cDNA clones and replicons, have been developed for a number of flaviviruses (A. A. Khromykh, et al., J. Virol. (1997) 71:1497-1505; M. S. Campbell, et al., Virol. (2000) 269:225-237; R. J. Hurrelbrink, et al., J. Gen. Virol. (1999) 80:3115-3125; M. Kapoor, et al., Gene (1995) 162:175-180; A. A. Khromykh et al., J. Virol. (1994) 68:4580-4588; C. J. Lai et al., Proc. Natl. Acad. Sci. U.S.A. (1991) 88:5139-5143; C. W. Mandl et al., J. Gen. Virol. (1997) 78:1049-1057; C. M. Rice et al., Science (1985) 229: 726-733; H. Sumiyoshi et al., J. Virol. (1992) 66:5425-5431; S. Polo et. al., J. Virol. (1997) 71:5366-5374), including lineage II WNV (V. F. Yamshchikov et al., Virology (2001) 281:294-304). Reporter genes can be engineered into the reverse genetics systems to allow for the monitoring of viral replication levels in the presence of potential inhibitors.

U.S. Patent Application Publication No. 2005/0058987 to Shi et al. describes high-throughput cell-based assays for the rapid screening and identification of potential inhibitors from compound libraries utilizing a reverse genetics system developed for lineage I WNV cDNA clone and lineage I WNV replicon.

WNV subgenomic RNAs capable of replicating within cells (replicons) have been reported. (Rossi 2005; Guo 2005). The replicon RNA genome typically contains the 5' Non-translated region (5' NTR), a portion of the Core coding region, a polyprotein encoding NS 1 through NS5, and the 3' NTR. Like replication of the WNV genome (reviewed in reference (Monath 2005)), in the replicon cells, the viral RNA dependent RNA polymerase, NS5B, in conjunction with other viral nonstructural proteins and possibly cell factors (Monath 2005), synthesize a minus strand RNA from the replicon subgenomic RNA template. The minus strand RNA in turn serves as templates for the synthesis of new genomic and message RNAs. Although data from studies of Kunjin virus suggest that both plus and minus strand RNA synthesis can occur in the absence of protein synthesis once the replication cycle establishes, viral protein synthesis is a prerequisite for replication of nascent RNAs (Guo 2005). In addition to a selectable marker, neomycin phosphotransferaser gene, which is used for selection of the stable cell line, a luciferase reporter gene was also inserted into the RNA with its translation driven by the EMCV IRES (Guo 2005, Monath 2005). The expression of the reporter gene depends on the replication of the replicon RNA and can be easily monitored for identification of antiviral compounds (Guo 2005).

For the purposes of drug screening it is preferable to use human epidemic-causing lineage I strains for assay setup to ensure that the identified compounds have a direct relevance to human disease.

Effective chemotherapeutics to treat WNV and other flaviviruses, known and emerging, are urgently needed. Although a limited number of inhibitors of flaviviruses have been identified, many of these have severe side effects, are not specific to flaviviruses, and are not known to be clinically effective and/or useful. For example, recent evidence suggested the use of nucleoside analogs as potential inhibitors of flaviviruses. Specific examples include inhibitors of orotidine monophosphate decarboxylase, inosine monophosphate dehydrogenase, and CTP synthetase. Although it appeared that these inhibitors may have been effective in virus infected Vero cells, their effectiveness in humans or animals (i.e., in vivo) is not known. Additionally, as these nucleoside analogs are broad-spectrum inhibitors of purine and pyrimidine biosynthesis, the occurrence of side effects and lack of flaviviral specificity would further limit their usefulness in a clinical setting.

Hepatitis B Virus (HBV) is a causative agent of acute and chronic liver disease including liver fibrosis, cirrhosis, inflammatory liver disease, and hepatic cancer that can lead to death in some patients. Although effective vaccines are available, there are still more than 300 million people worldwide, i.e., 5% of the world's population, chronically infected with the virus (Locamini, S. A., et. al., Antiviral Chemistry & Chemotherapy (1996) 7(2):53-64). Such vaccines have no therapeutic value for those already infected with the virus. In Europe and North America, between 0.1% to 1% of the population is infected. Estimates are that 15% to 20% of individuals who acquire the infection develop cirrhosis or another chronic disability from HBV infection. Once liver cirrhosis is established, morbidity and mortality are substantial, with about a 5-year patient survival period (Blume, H., E., et. al., Advanced Drug Delivery Reviews (1995) 17:321-331). It is therefore necessary and of high priority to find improved and effective anti-HBV anti-hepatitis therapies.

Other hepatitis viruses significant as agents of human disease include Hepatitis A, Hepatitis B, Hepatitis C, Hepatitis Delta, Hepatitis E, Hepatitis F, and Hepatitis G (Coates, J. A. V., et. al., Exp. Opin. Ther. Patents (1995) 5(8):747-756). In addition, there are animal hepatitis viruses that are species-specific. These include, for example, those infecting ducks, woodchucks, and mice.

WO 2001/10429A2 to Dwek et al. describes methods of inhibiting morphogenesis of a pestivirus or flavivirus and treatment of hepatitis B and C infection by administration of a long chain N-alkyl amino or imino compound or an oxa-substituted derivative thereof including N-(7-oxa-nonyl)-1,5-dideoxy-1,5-imino-D-galactitol.

US 2006/0074107A1 to Butters et al. describes an agent capable of increasing the rate of neuronal glycolipid degradation for the treatment of mucopolysaccharide diseases having the following formula

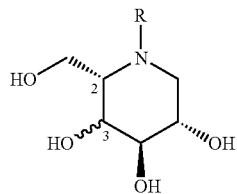

wherein R is $C_{1-16}$ straight or branched-chain alkyl, optionally substituted by $C_{3-7}$ cycloalkyl, and optionally interrupted by —O—, the oxygen being separated from the ring nitrogen by at least two carbon atoms, or $C_{1-10}$ alkylaryl where aryl is phenyl, pyridyl, thienyl or furyl wherein phenyl is optionally substituted by one or more substituents selected from F, Cl, Br, $CF_3$, $OCF_3$, $OR^1$ and $C_{1-6}$ straight or branched-chain alkyl; and $R^1$ is hydrogen, or $C_{1-6}$ straight or branched-chain alkyl.

U.S. Pat. No. 6,809,083 to Mueller et al. described the use of N-substituted-1,5-dideoxy-1,5-imino-D-glucitol compounds for treating hepatitis virus infections. However, Mueller et al. did not describe using N-substituted alkylhydroxyl-cycloalkyl derivatives.

1,5-dideoxy-1,5-imino-D-glucitol (also known as 1-deoxynojirimycin, DNJ) and its N-alkyl derivatives (together, "imino sugars") are known inhibitors of the N-linked oligosaccharide processing enzymes alpha glucosidase I and II (Saunier et al., J. Biol. Chem. (1982) 257:14155-14161 (1982); Elbein, Ann. Rev. Biochem. (1987) 56:497-534). As glucose analogs, they also have potential to inhibit glucose transport, glucosyl-transferases, and/or glycolipid synthesis (Newbrun et al., Arch. Oral Biol. (1983) 28: 516-536; Wang et al., Tetrahedron Lett. (1993) 34:403-406). Their inhibitory activity against glucosidases has led to the development of these compounds as anti-hyperglycemic agents and antiviral agents. See, for example, PCT International Publication WO 87/03903 and U.S. Pat. Nos. 4,065,562; 4,182,767; 4,533,668; 4,639,436; 4,849,430; 4,957,926; 5,011,829; and 5,030,638.

Glucosidase inhibitors such as N-alkyl-1,5-dideoxy-1,5-imino-D-glucitol compounds wherein the alkyl group contains between three and six carbon atoms have been shown to be effective in the treatment of Hepatitis B infection (PCT International Publication WO 95/19172). For example, N-(n-butyl)deoxynojirimycin (N-butyl-DNJ; N-(n-butyl)-1-5-dideoxy-1,5-imino-D-glucitol) is effective for this purpose (Block, T. M., Proc. Natl. Acad. Sci. USA (1994) 91:2235-2239; Ganem, B. Chemtracts: Organic Chemistry (1994) 7(2), 106-107). N-butyl-DNJ has also been tested as an anti-HIV-1 agent in HIV infected patients.

The deoxynojirimycins (DNJs) are iminocyclitol glucomimetics that inhibit ER glucosidases by competing with glucose (Tan et al., 1991). Although millimolar amounts of DNJ are needed to achieve substantial inhibition of the endoplasmic reticulum (ER) enzyme in tissue culture and to achieve 50% inhibition of virus yields against sensitive viruses, the drug is well tolerated with little apparent cytotoxicity. Modification of DNJs by adding side chains to the ring nitrogen atom has been shown to affect their activity and toxicity. For example, N-nonyl-DNJ (NNDNJ), a nine carbon alkyl side chain derivative of DNJ (FIG. 1) was shown to be an effective antiviral agent against HBV (Block et al., 1994) and BVDV (Durantel et al., 2001; Jordan et al., 2002; Zitzmann et al., 1999). However, NNDNJ possessed more toxic activity (Mehta et al., 2001; Zitzmann et al., 1999) and had a selectivity index that was deemed to be too narrow for clinical development. Therefore, compounds with similar efficacy but better toxicity profiles were sought.

Despite the current developments, there is a need in the art for novel flavivirus replication inhibitors, particularly, non-nucleoside based compounds, which have better toxicity profiles.

All references cited herein are incorporated herein by reference in their entireties.

SUMMARY OF THE INVENTION

Inventors discovered novel broad spectrum antiviral molecules, iminosugar compounds, iminocyclitol derivatives, having activity against enveloped virus. Iminosugars are small molecules that inhibit the cellular glucosidase and hence affect the glycoprotein processing during virus life cycle. Exemplary flaviviruses include Bovine Diarrhea virus (BVDV), West Nile virus (WNV), Dengue virus (DV) and Hepatitis B virus (HBV).

Accordingly, one aspect, of invention provides a compound of formula (I)

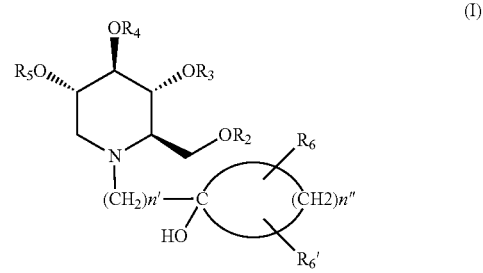

wherein $R^2$, $R^3$, $R^4$ and $R^5$ are the same or different and are selected from the group consisting of hydrogen, acyl, benzyl, alkyl, aryl, sulfonyl, phosphonyl, silyl, $R_6$ is at least one of alkyl or branched alkyl, heteroalkyl or aryl, $R_6'$ is a bridging group selected from at least one of bicycle[2.2.1]heptyl, bicycle[3.2.1]octyl, oxa analogs, admonyl and cubyl, n'=2-10, n"=1-10, enantiomers and stereoisomers of said compound and physiologically acceptable salts or solvates of said compound, enantiomer or stereoisomer.

Other embodiments provide an anti-viral compound as shown by formula (I) or its variants.

Further aspects provide a method for inhibiting production of a virus belonging to the Flaviviridae family comprising contacting a mammalian cell infected by said virus with an effective amount of an anti-viral composition comprising the anti-viral compound of formula (I) or its variants.

Additional embodiments relate to pharmaceutical compositions, comprising an antiviral effective amount of at least one N-substituted-1,5-dideoxy-1,5-imino-D-glucitol compound of Formula I or a pharmaceutically acceptable salt thereof, as above, and a pharmaceutically acceptable carrier, excipient, or diluent.

In a preferred embodiment, the N-substituted-1,5-dideoxy-1,5-imino-D-glucitol compound is N-pentyl(1-hydroxycyclohexyl)-1,5-dideoxy-1,5-imino-D-glucitol (N-pentyl(1-hydroxycyclohexyl)-DNJ (OSL-95II)) of formula (III)

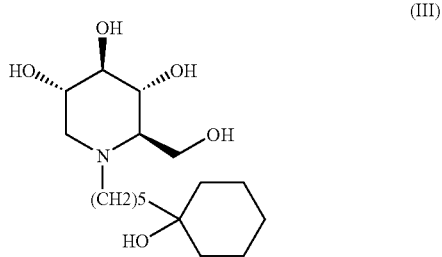

(III)

possess activity against a number of viruses tested including BVDV, West Nile and Hepatitis B virus.

In another preferred embodiment, the 1,5-dideoxy-1,5-imino-D-glucitol derivative compound is N-butyl(1-hydroxycyclohexyl)-1,5-dideoxy-1,5-imino-D-glucitol and has the general formula (IV):

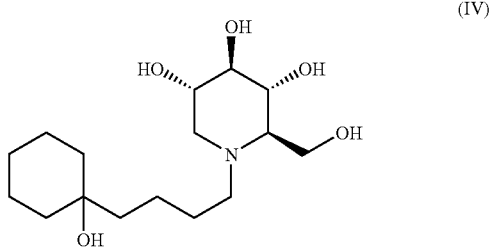

(IV)

possess activity against a number of viruses tested including BVDV, West Nile and Hepatitis B virus.

In another preferred embodiment, the 1,5-dideoxy-1,5-imino-D-glucitol derivative compound is N-hexyl(1-hydroxycyclohexyl)-1,5-dideoxy-1,5-imino-D-glucitol and has the general formula (V):

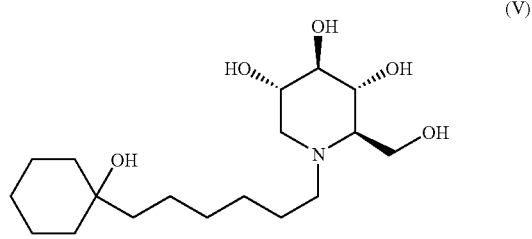

(V)

possess activity against a number of viruses tested including BVDV, West Nile and Hepatitis B virus

For control, DMSO was used in place of compounds. Plaques from drug treated samples were expressed % of DMSO control on Y-axis.

Figure 5:
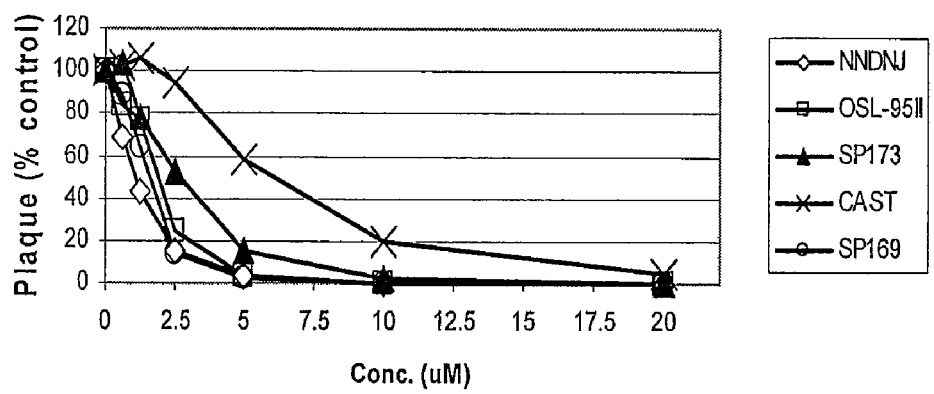
FIG. 5A is a graph demonstrating antiviral activity against DV. BHK cells were infected with DV serotype 2 in the presence of the indicated concentrations of the five compounds. After three days, the virus released into the media was quantified on Vero cells under the tragacanth overlay as described in the Materials and Methods. The experiment was done in duplicate wells and the average values were plotted.
Figure 5:
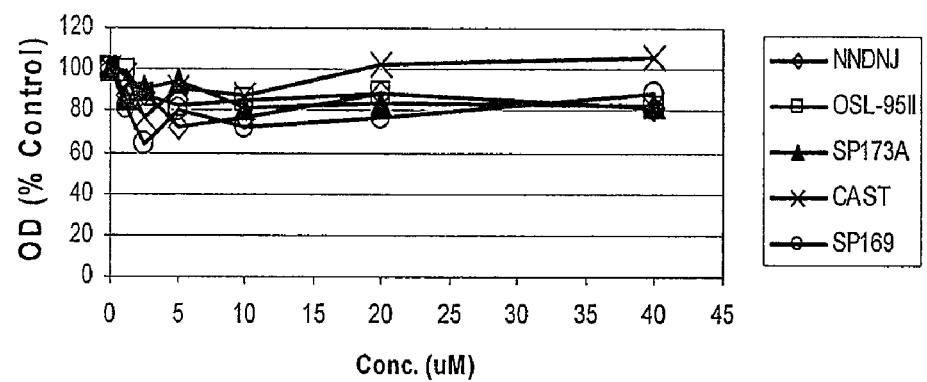

FIG. 5B is a graph demonstrating compound cytotoxicity, which was assessed in parallel cell plates by MTT assay and the OD reading at 570 nm was represented on the Y axis as % of DMSO control.

Figure 6:
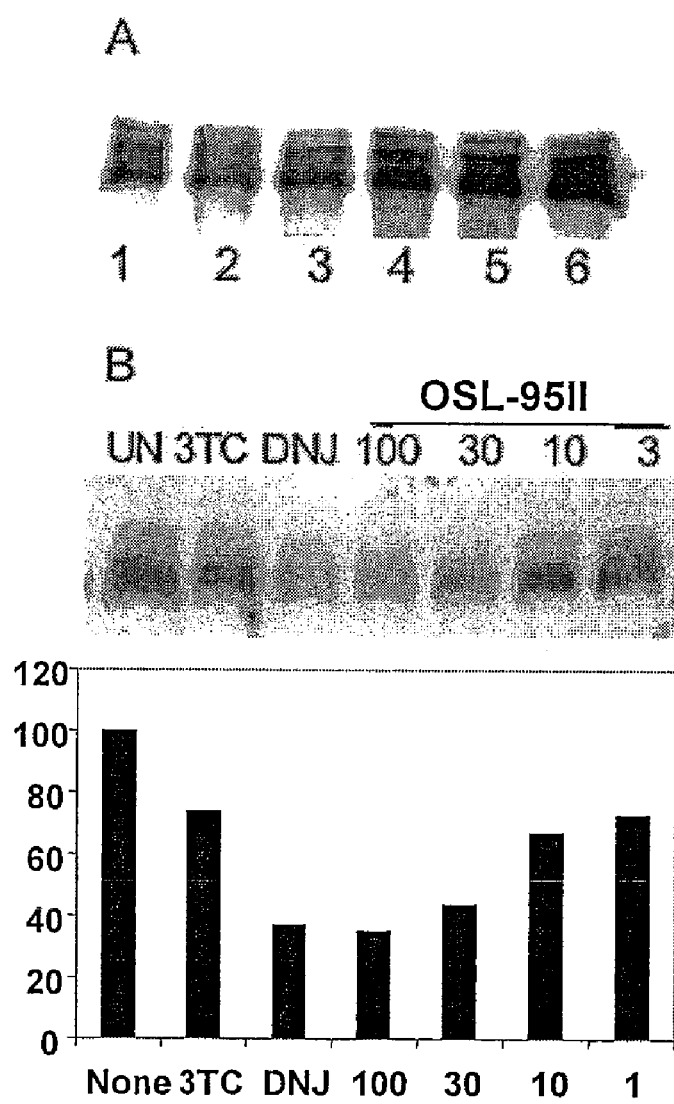

FIGS. 6(A and B) are graphs demonstrating variable activity of N-alkylcycloalkyl-DNJ compounds against HBV. In FIG. 6A, HepG2.2.15 cells were untreated (lanes 1 and 2) or treated for 7 days with 50 uM N-butylcyclohexyl-DNJ (SP169) (lanes 3 and 4), or 50 uM N-pentylcyclohexyl-DNJ (OSL-1) (lanes 5 and 6). Both LHBs and MHBs are detected by immunoblotting using antibody that recognizes pre-S2. In FIG. 6B, cells were untreated or were treated for 7 days with 3TC (1 ug/ml), DNJ (6 mM), or N-pentyl(1-hydroxy-cyclohexyl)-DNJ (OSL-95II) at the indicated concentrations. The lower portion of this figure shows densitometric quantiation of the immunoblot, which was probed as in panel A.

DETAILED DESCRIPTION OF ILLUSTRATIVE EMBODIMENTS

Aspects of the invention relate to pharmaceutical compositions and methods of treating virus infections, especially those caused by BVDV, HBV, WNV, and DV in humans, other mammals, and cells using N-substituted-1,5-dideoxy-1,5-imino-D-glucitol compounds alone or in combination with either an antiviral nucleoside, an antiviral nucleotide, mixtures thereof, and/or an immunomodulating or immunostimulating agent and other pharmaceutically acceptable agents. The N-substituted-1,5-dideoxy-1,5-imino-D-glucitol compounds have basic nitrogen atoms and may be used in the form of a pharmaceutically acceptable salt. Nucleosides and nucleotides can be substituted purine or pyrmidine heterocycles. The immunomodulating and immunostimulating agents can be used, which include those that stimulate immune responses effective in controlling or eliminating viruses or other infectious agents. Non-limiting examples of such immunomodulating and immunostimulating agents include cytokines, peptide agonists, steroids, and classic drugs such as levamisol.

Pharmaceutical compositions may be provided to a cell or cells, or to a human or other mammalian patient, either in separate, pharmaceutically acceptable formulations administered simultaneously or sequentially, formulations containing more than one therapeutic agent, or by an assortment of single agent and multiple agent formulations. However administered, these pharmaceutical compositions form an anti-virus effective amount of components.

As used herein, the term "effective amount" refers to an amount of an N-substituted-1,5-dideoxy-1,5-imino-D-glucitol compound alone, or a combined amount of (1) an N-substituted-1,5-dideoxy-1,5-imino-D-glucitol compound with either an antiviral nucleoside, an antiviral nucleotide, a mixture of an antiviral nucleoside and an antiviral nucleotide, or an immunomodulating/-immunostimulating agent (or mixtures thereof), or (2) a combined amount of an N-substituted-1,5-dideoxy-1,5-imino-D-glucitol compound with an antiviral nucleoside, an antiviral nucleotide, or a mixture thereof, and an immunomodulating/-immunostimulating agent (or mixtures thereof) effective in treating hepatitis virus infection. The antiviral effectiveness of the aforementioned combinations may involve a variety of different phenomena associated with viral replication and assembly. These may include, for example, blocking viral DNA synthesis; blocking viral transcription; blocking virion assembly; blocking virion release or secretion from infected cells; blocking or altering viral protein function, including the function of viral envelope protein(s); and/or the production of immature or otherwise non-functional virions. The overall effect is an inhibition of viral replication and infection of additional cells, and therefore inhibition of the progress of infection in the patient.

The terms "alkoxy" and "alkyloxy" embrace linear or branched oxygen-containing radicals each having alkyl portions of one to about ten carbon atoms. Alkoxyalkyl groups ("alkylether" or "oxa" derivatives) in some aspects can be $C_3$ to $C_{20}$, preferably $C_5$ to $C_{16}$, wherein one to five non-terminal carbon atoms, preferably one to three non-terminal carbon atoms, more preferably one to two non-terminal carbon atoms, most preferably one non-terminal carbon atom, can be replaced with oxygen.

The term "aryl", alone or in combination with another radical, means a carbocyclic aromatic system containing one, two or three rings wherein such rings may be attached together in a pendent manner or may be fused. The term "aryl" embraces aromatic radicals such as, for example, phenyl, naphthyl, tetrahydronaphthyl, indyl, and biphenyl.

The term "arylalkyl" embraces aryl-substituted alkyl radicals such as benzyl, diphenylmethyl, triphenylmethyl, phenylethyl, and diphenylethyl.

The term "cycloalkyl" embraces saturated carbocyclic radicals having three to about twelve carbon atoms. More preferred cycloalkyl radicals are "lower cycloalkyl" radicals having three to about eight carbon atoms. Examples of such radicals include cyclopropyl, cyclobutyl, cyclopentyl and cyclohexyl. "Cycloalkylalkyl" means an alkyl group susbstituted with a cycloalkyl group.

The term "acyl" denotes a radical provided by the residue after removal of hydroxyl from an organic acid. Examples of such acyl radicals include alkanoyl and aroyl radicals. "Alkanoyl" means branched or straight chain alkanecarbonyl having a chain length of $C_1$ to $C_{20}$, preferably $C_1$ to $C_{10}$, more preferably $C_1$ to $C_5$; "aroyl" means arylcarbonyl; and "trifluoroalkanoyl" means alkanoyl containing three fluoro substituents. Examples of such alkanoyl radicals include formyl, acetyl, propionyl, butyryl, isobutyryl, valeryl, isovaleryl, pivaloyl, hexanoyl, and radicals formed from succinic, glycolic, gluconic, lactic, malic, tartaric, citric, ascorbic, glucuronic, maleic, fumaric, pyruvic, mandelic, pantothenic, .beta.-hydroxybutyric, galactaric and galacturonic acids.

When used in combination with another radical when referring to the imino sugars, the term "alkyl" means a straight or branched chain hydrocarbon radical containing from 1 to about 20 carbon atoms, preferably 1 to about 16 carbon atoms, more preferably from about 2 to about 12 carbon atoms, more preferably from about 3 to about 10 carbon atoms.

The term "alkenyl" embraces radicals having "cis" and "trans" orientations, or alternatively, "E" and "Z" orientations. The term "alkynyl" embraces linear or branched radicals having at least one carbon-carbon triple bond of two to about twenty carbon atoms or, preferably, two to about twelve carbon atoms. More preferred alkynyl radicals are "lower alkynyl" radicals having two to about six carbon atoms. Examples of alkynyl radicals include propargyl, 1-propynyl, 2-propynyl, 1-butyne, 2-butenyl and 1-pentynyl.

The term "cycloalkylalkyl" embraces alkyl radicals substituted with a cycloalkyl radical. Preferred cycloalkylalkyl radicals are $C_4$ to $C_{20}$; more preferred cycloalkylalkyl radicals are $C_4$ to $C_{18}$ "lower cycloalkylalkyl" which embrace lower alkyl radicals substituted with a lower cycloalkyl radical as defined above. Examples of such radicals include cyclopropylmethyl, cyclobutylmethyl, cyclopentylmethyl and cyclohexylmethyl.

Inventors have discovered N-substituted alkylhydroxylcycloalkyl derivatives of N-substituted-1,5-dideoxy-1,5-imino-D-glucose compounds (DNJ), which exhibit activity against BVDV, WNV, DV, and hepatitis virus (e.g., HBV). N-substituted alkylhydroxylcycloalkyl derivative are depicted by the formula (I) below:

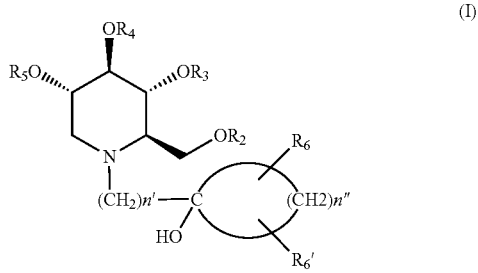
(I)

wherein $R^2$, $R^3$, $R^4$ and $R^5$ are the same or different and are selected from the group consisting of hydrogen, acyl, benzyl, alkyl, aryl, sulfonyl, phosphonyl, silyl, $R_6$ is at least one of alkyl or branched alkyl, heteroalkyl or aryl, $R_6'$ is a bridging group selected from at least one of bicycle[2.2.1]heptyl, bicycle[3.2.1]octyl, oxa analogs, admonyl and cubyl, n'=2-10, n"=1-10, enantiomers and stereoisomers of said compound and physiologically acceptable salts or solvates of said compound, enantiomer or stereoisomer.

In a preferred embodiment, $R^2$, $R^3$, $R^4$ and $R^5$ are hydrogen and N-substituted alkylhydroxylcycloalkyl derivative are depicted by the formula (IA) below:

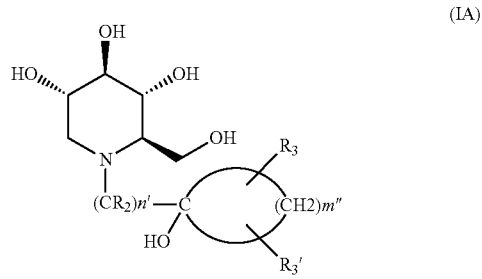
(IA)

wherein $R_2$ is methyl or straight chain alkyl, $R_3$ is alkyl or branched alkyl, heteroalkyl or aryl, $R'_3$ is a bridging group, such as, for example, bicycle[2.2.1]heptyl, bicycle[3.2.1]octyl and oxa analogs as well as admonyl and cubyl, m"=1-10, n'=2-10.

The deoxynojirimycin moiety (DNJ) is derived from 1,5,-dideoxy-1,5-imino-D-glucitol, a piperidine derivative, and is depicted by the formula (II) below

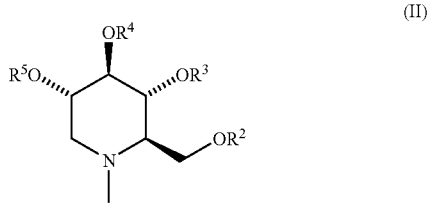
(II)

wherein $R^2$, $R^3$, $R^4$ and $R^5$ are the same or different and are selected from the group consisting of hydrogen, acyl, benzyl, alkyl, aryl, sulfonyl, phosphonyl, and silyl.

Embodiments comprise any stereoisomeric forms of compounds of formula (I). Compounds of formula (I) can have one or more asymmetric carbons. Those skilled in the art that understand those imino sugars having asymmetric carbon atoms may exist in diastereomeric, racemic, or optically active forms. Various aspects of the invention relate to all of these forms, and more specifically, include enantiomers, diastereomers, racemic mixtures, and other mixtures thereof.

Preferred examples of derivatives of formula (I) include:

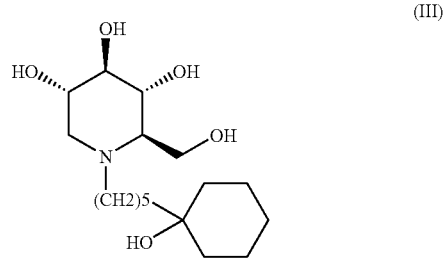
(III)

N-pentyl(1-hydroxycyclohexyl)-DNJ (OSL-95II) or N-pentyl(1-hydroxycyclohexyl)-1,5-dideoxy-1,5-imino-D-glucitol.

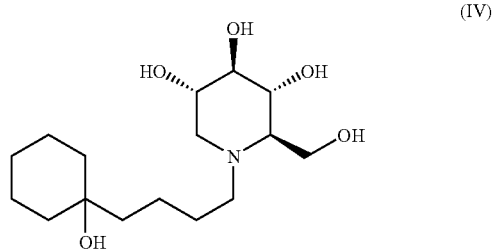
(IV)

N-butyl(1-hydroxycyclohexyl)-DNJ (OSL-12-31) or N-butyl(1-hydroxycyclohexyl)-1,5-dideoxy-1,5-imino-D-glucitol

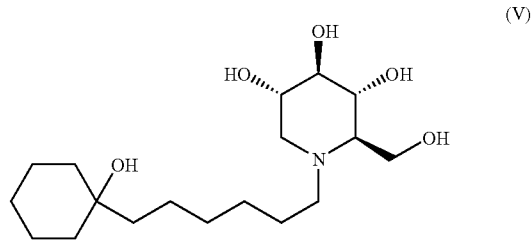
(V)

N-hexyl(1-hydroxycyclohexyl)-1,5-dideoxy-1,5-imino-D-glucitol (OSL-3).

Figure 4:
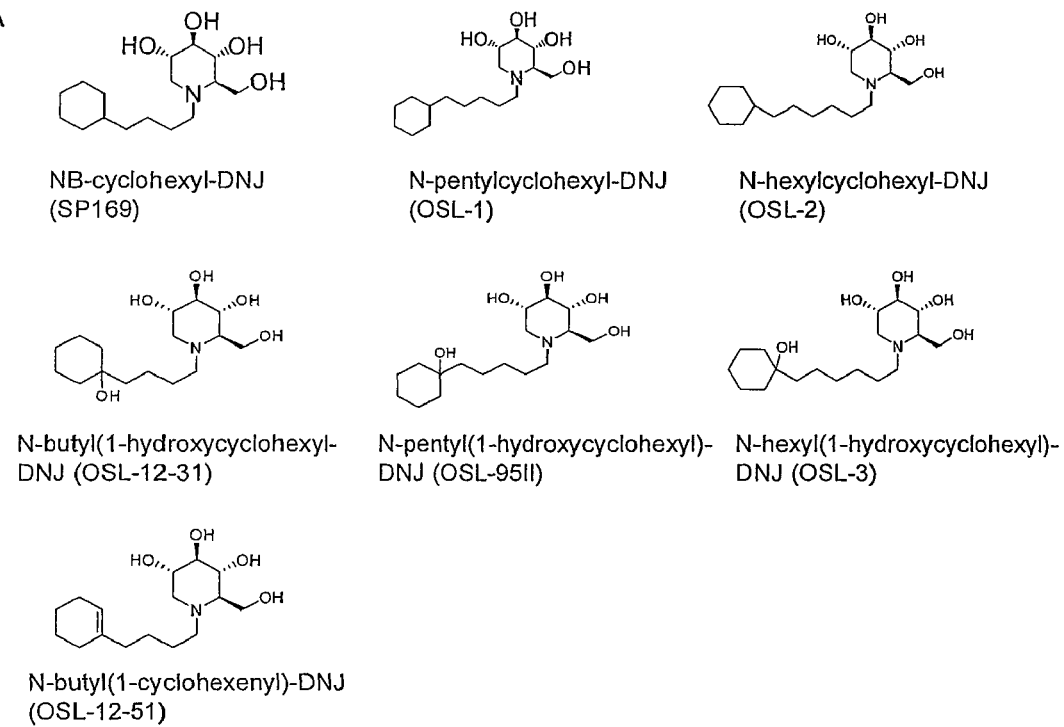
FIG. 4A is a structure of alkylcylcoalkyl-DNJs.
FIG. 4B is a graph demonstrating antiviral activity of N-butylcyclohexyl-DNJ (SP169) and N-propylcyclohexyl-DNJ (SP173) against WNV. Toxicity of the compounds was assayed by using MTT assays on MDBK cells after 72-hour drug treatment. The MTT OD reading at 570 nm from cells treated with the compounds are compared with that from DMSO treated cells and were shown as % DMSO control on the Y axis.
FIG. 4C is a graph demonstrating antiviral activity of the compounds against BVDV was tested in MDBK cells in a yield reduction assay as described in Materials and methods. All experiments were done in duplicates and the average data from a typical experiment was plotted. The number of plaques in drug-treated cells was compared with DMSO-treated cells and plotted on the y-axis as % control.
FIG. 4D is a graph demonstrating antiviral activity and cytotoxicity against WNV in BHK cells. BHK cells in 96 wells ($2.5 \times 10^4$ cells/well) were infected with WNV at an moi of 0.05 and incubated in the presence of the indicated concentrations of compounds. After 48 hours, the virus released into the media was quantified by plaque assay. Compound cytotoxicity was measured by using MTT assay at the same time on cells in parallel plates. Y axis: the effect of compound on plaques numbers or absorption in comparison to DMSO controls were shown in balck and open bar, respectively. The experiment was done in duplicates and the average data was plotted.
Figure 4B:
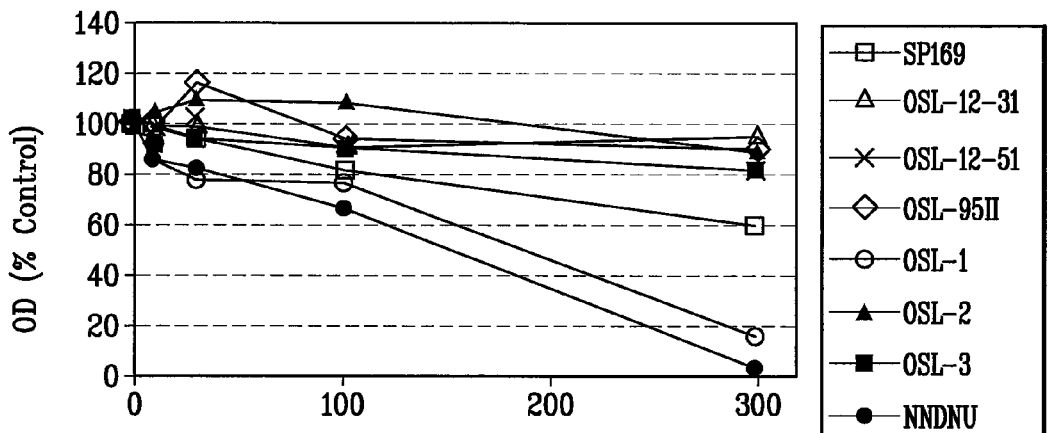
Figure 4C:
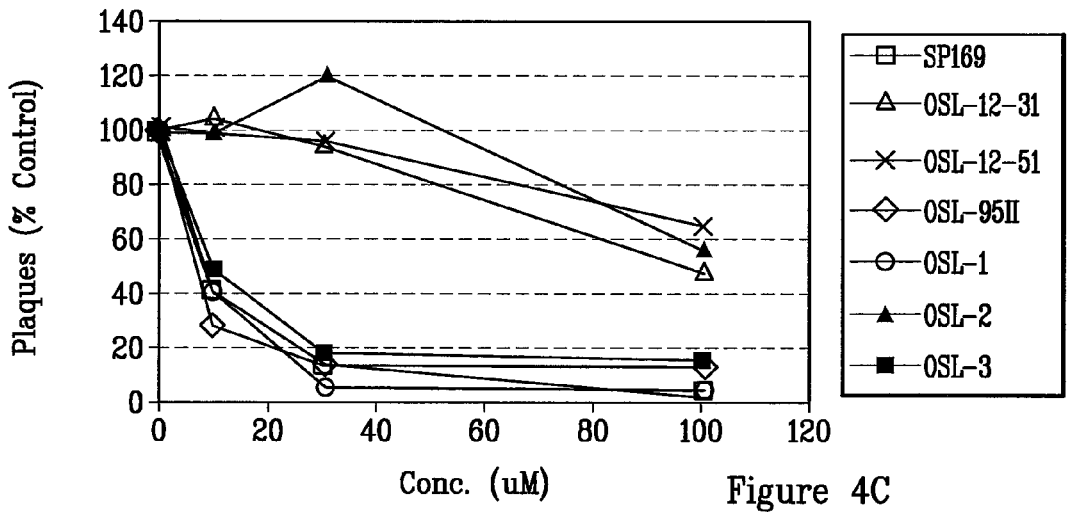

Compounds with alkylcycloalkyl side chains that also contain hydroxyl were synthesized and tested for antiviral and cytotoxicity profiles. Compounds N-butylcyclohexyl-DNJ (SP 169), N-butyl(1-cyclohexenyl)-DNJ (OSL-12-51) and N-butyl(1-hydroxylcyclohexyl)-DNJ (OSL-12-31) are molecules with DNJ head groups and 4 carbon side chains terminating in cyclohexyl rings containing either no modification, a double bond cyclohexenyl or a hydroxyl group, respectively (FIG. 4A). Although N-butyl (1-cyclohexenyl)-DNJ (OSL-12-51) and N-butyl (1-hydroxylcyclohexyl)-DNJ (OSL-12-31) were well tolerated by the cultures with CC50 values of greater than 300 uM (FIG. 4B), they were each substantially less active against BVDV compared with N-butylcyclohexyl-DNJ (SP169) (FIG. 4C). It is noted, however, that OSL-12-31 was less toxic in MDBK cultures than SP169, suggesting that hydroxylation of the cyclohexyl ring might be beneficial.

Two DNJ compounds similar to N-butylcyclohexyl-DNJ (SP 169) but with longer side chains were synthesized. N-pentylcyclohexyl-DNJ (OSL-1) and N-pentyl(1-hydroxylcyclohexyl)-DNJ (OSL-95II) are DNJs with 5 carbon length side chains terminating in cyclohexyl rings or a hydroxyl at the first ring carbon, respectively. In MDBK cells, N-pentyl (1-hydroxycyclohexyl)-DNJ (OSL-95II) is much less toxic than N-pentylcyclohexyl-DNJ (OSL-1) (FIG. 4B). Both compounds were tested against BVDV in virus yield reduction assay and were shown to have similar antiviral activity in the BVDV antiviral assay (FIG. 4C).

Figure 4D:
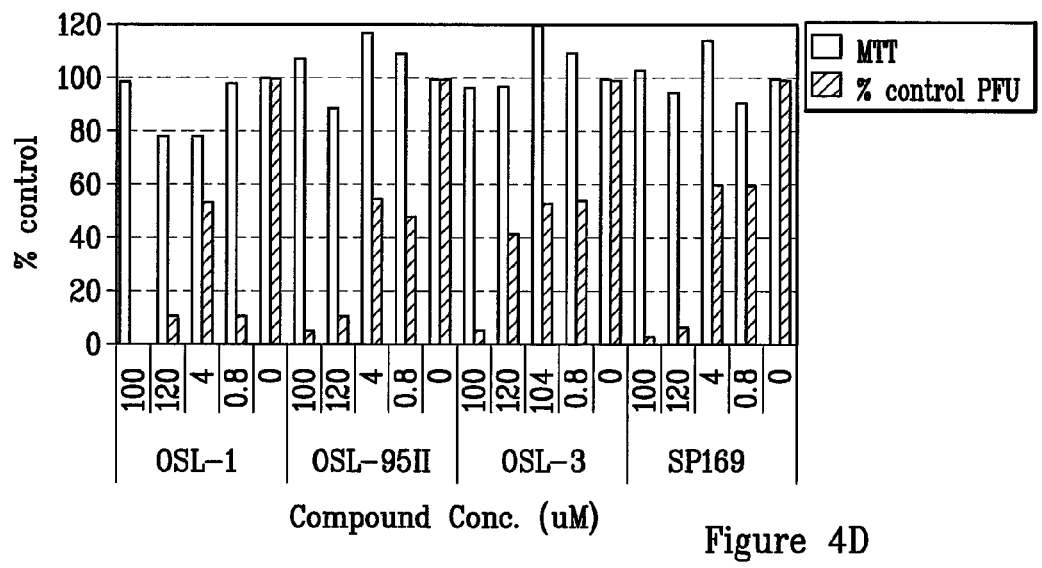

The two compounds were then tested for antiviral activity against WNV. As shown in FIG. 4D, both compounds had similar antiviral activity against WNV. Thus, both N-pentyl (1-hydroxycyclohexyl)-DNJ (OSL-95II) and N-pentylcyclohexyl-DNJ (OSL-1) were potent inhibitors against BVDV and WNV as compared to N-butylcyclohexyl-DNJ (SP169) (Table 1).

TABLE 1

| Compound | BVDV (MDBK) | | | WNV (BHK) | | | DV (BHK) | |
| --- | --- | --- | --- | --- | --- | --- | --- | --- |
|  | CC50$^a$ | IC50$^b$ | SI$^c$ | CC50 | IC50 | SI | IC50 | SI |
| NNDNJ | 150 | <3 | >50 | 20-100 | 4 | 5-25 | 1 | 20-100 |
| OSL-95II | >500 | 3 | >166 | >100 | 4.5 | >9 | 2 | >50 |
| SP173 | >150 | 5 | >30 | >100 | 1 | >100 | 3 | >33 |
| SP169 | 300 | 3 | >100 | >100 | 2.5 | >40 | 1.5 | >66 |
| CAST |  |  |  | >100 | >20 | 5 | 6 | >17 |

Table 1 is a summary of antiviral activity against BVDV, WNV and DV for N-butylcyclohexyl-DNJ (SP 169), N-propylcyclohexyl-DNJ (SP173) and N-pentyl(1-hydroxycyclohexyl)-DNJ (OSL-95II) in comparison with NNDNJ and Castanospermine. The data in the table represent average value of duplicate assays in a typical experiment. a. CC50: concentration of compound that reduced MTT values (read at 570 nm) by 50%, relative to DMSO treated controls. b. IC50: concentration of the compound that reduced the amount of virus (plaque number) by 50%, relative to DMSO treated controls. c. SI: Selective Index, the value of CC50/IC50.

The reduced cytoxicity of N-pentyl(1-hydroxycyclohexyl)-DNJ (OSL-95II) was observed. N-pentyl(1-hydroxycyclohexyl)-DNJ (OSL-95II) was significantly less cytotoxic against MDBK cells than even N-butylcyclohexyl-DNJ (SP169); consistent with the notion that hydroxylation of the cyclohexyl ring reduces toxicity, as was observed with N-butyl(1-hydroxylcyclohexyl)-DNJ (OSL-12-31). However, unlike N-butyl(1-hydroxylcyclohexyl)-DNJ (OSL-12-31), which is a 4 carbon side chain DNJ and possesses the same cyclohexyl ring structure as does N-pentyl(1-hydroxycyclohexyl)-DNJ (OSL-95II), the later remains as active as N-butylcyclohexyl-DNJ (SP 169).

Since both 4 and 5 carbon length side chain cyclohexyl-containing DNJs were antiviral and well tolerated, 6 carbon side versions were synthesized and tested. N-hexylcyclohexyl-DNJ (OSL-2) and N-hexyl(1-hydroxycyclohexyl)-DNJ (OSL-3) were synthesized and studied (FIG. 4A). Both compounds were well tolerated in the MDBK cells, with CC50s greater than 300 uM (FIG. 4B). However, although N-hexyl(1-hydroxycyclohexyl)-DNJ (OSL-3) was as effective against BVDV and WNV as the other compounds in this series tested, surprisingly, N-hexylcyclohexyl DNJ (OSL-2) appeared to be inactive against BVDV (and was therefore not tested against WNV) (FIGS. 4C & D). That is, despite having the same 6 carbon length side chain as the anti-BVDV and WNV active OSL-3, OSL-2 lost all detectable antiviral activity.

A few of the more potent conformationally restricted side chain compounds were also investigated against DV for the possibility of possessing a more broad spectrum antiviral activity. In the DV infection assay, a serotype 2 DV was used to infect BHK cells in the presence or absence of testing compounds and viruses produced after 72 hours were titered in a manner similar to the WNV assay. In this experiment, N-butylcyclohexyl-DNJ (SP169), N-pentyl(1-hydroxylcyclohexyl)-DNJ (OSL-95II), N-butylcyclohexyl-DNJ (SP169) and N-propylcyclohexyl-DNJ (SP173) were compared with NNDNJ (Wu et al., 2002) and castanospermine. FIG. 5A shows that as expected, NNDNJ had potent activity against DV, with an IC50 of 1 uM. Castanospermine, on the other hand, was less active with an IC50 of 6 uM. All three iminocyclitol with conformation locking side chains, N-butylcyclohexyl-DNJ (SP169), N-propylcyclohexyl-DNJ (SP173) and N-pentyl(1-hydroxycyclohexyl)-DNJ (OSL-95II), significantly inhibited DV production with IC50's between 1 and 2 uM. All of these compounds are more potent against DV than against WNV. All compounds had no toxicity at the highest concentrations used in this experiment (FIG. 5B, Table 1).

Although N-butylcyclohexyl-DNJ (SP169) and N-pentyl (1-hydroxycyclohexyl)-DNJ (OSL-95II) were considerably more potent against BVDV and WNV than was DNJ, it was of interest to determine whether these compounds had detectable in vitro antiviral activity against HBV. MHBs and LHBs are HBV envelope proteins that are sensitive to glucosidase inhibition and inhibition of these important viral glycoproteins serves as a surrogate for HBV growth. This surrogate assay is used because HBV does not readily infect tissue cultures, and single step growth analysis is not possible. Previously, it was established that N-butylcyclohexyl-DNJ (SP169) could reduce secretion of the MHBs (IC50≦35 uM), when it was expressed transiently in cells (Norton et al., 2005). To assess the activity of this compound in the context of viral replication, HepG2 2.2.15 cells were incubated with the indicated DNJ derived compound. HepG 2.2.15 cells secrete readily detectable amounts of MHBs and LHBs into the culture medium. After 7 days of incubation, the amount of HBV M and L in the culture medium was determined by western blot. Surprisingly, N-butylcyclohexyl-DNJ (SP169) was unable to inhibit secretion of viral glycoproteins at 50 uM, in contrast to the situation with BVDV and WNV. The related compound N-pentylcylcohexyl-DNJ (OSL-1) also lacked antiviral activity in this assay (FIG. 6A). The nature of the selective antiviral activity is not known, but may be due to cell specific activity since HBV is studied in human liver derived hepatoblastoma HepG2 cells and BVDV and WNV were studied in MDBK and BHK cells, respectively.

Since N-pentyl(1-hydroxycyclohexyl)-DNJ (OSL-95II) had comparable anti-BVDV and WNV activity as N-butylcyclohexyl-DNJ (SP169), it was of interest to determine if N-pentyl(1-hydroxycyclohexyl)-DNJ (OSL-95II) possessed any activity against HBV in the HepG2.2.15 cell assay. In contrast to N-butylcyclohexyl-DNJ (SP169), three batches of independently synthesized N-pentyl(1-hydroxycyclohexyl)-DNJ (OSL-95II) was nearly as effective in reducing the amount of MHBs and LHBs detected in the culture medium at 30 uM as was DNJ at 6000 uM (FIG. 6B). The 6000 uM concentration is the amount of DNJ needed to inhibit at least 90% of the ER glucosidase, and antiviral activity at this dose is consistent with previous findings (Mehta et al., 2001). 3TC, a nucleoside analog inhibitor of the viral polymerase had little effect. The result showed that N-pentyl(1-hydroxycyclohexyl)-DNJ (OSL-95II) is a much better inhibitor for HBV than N-butylcyclohexyl-DNJ (SP169).

Synthesis of DNJ derivatives has been described in prior art, see for example, U.S. Pat. Nos. 6,465,487, 6,927,294, 5,622,972, 4,246,345, 4,266,025, 4,405,714, 4,805,650, 5,401,645. The compound 1,5-dideoxy-1,5-imino-D-glucitol is alternatively referred to herein as "deoxynojirimycin" or simply "DNJ." DNJ is well known and commercially available from a variety of chemical manufacturers, e.g., ICN Biochemicals Inc., Costa Mesa, Calif. (Cat. #150819); Chemical Dynamics Corporation, South Plainfield, N.J. (Cat. #26-9415-00). DNJ derivatives with N-alkyl side chains can be produced by way of reductive amination with RCHO/H2/Pd—C upon DNJ.

The free hydroxyl groups on 1,5-dideoxy-1,5-imino-D-glucitol and the N-substituted derivatives thereof may preferably be acylated with up to four, preferably exactly four, O-acyl groups. It is presently preferred to provide the compounds as the peracylated derivatives. O-acylated 1,5-dideoxy-1,5-imino-D-glucitol and its N-substituted derivatives may be referred to as "prodrugs". The O-acyl groups are enzymatically removed to provide the non-O-acylated (i.e., hydroxy-containing N-substituted or unsubstituted 1,5-dideoxy-1,5-imino-D-glucitol compounds) in vivo. M. Bryant et al., 10th International Conference of AIDS, Berlin, Jun. 7-11, 1993, Abstr. No. WS-A11-2.

With respect to the O-acyl groups, $R^2$, $R^3$, $R^4$ and $R^5$ may individually be an acyl moiety represented by the formula

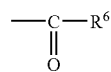

wherein $R^6$ is a linear or branched $C_1$-$C_{10}$ alkyl moiety including but not limited to methyl, ethyl, propyl, isopropyl, butyl, pentyl, hexyl, nonyl, a $C_3$-$C_7$ cycloalkyl, or a $C_4$-$C_{10}$ cycloalkylalkyl including but not limited to (cyclopropyl)methyl, (cyclopropyl)ethyl, (cyclobutyl)ethyl, (cyclopentyl)ethyl, (cyclohexyl)methyl, (cyclohexyl)ethyl and the like.

The DNJ portion of the compound of formula (I) can be modified as described in U.S. Pat. Nos. 6,689,759 to Jacob et al., 6,465,487 to Block et al., 6,465,488 to Butters et al., 6,809,083 to Mueller et al., 6,927,294 to Petasis et al., 5,103,008, 5,451,679 and 5,595,981 to Barta et al.

The N-substituted-imino-D-glucitol compounds, including prodrugs, useful in certain aspects of the invention, can be prepared by methods well known in the art. For example, Example 13 of U.S. Pat. No. 5,144,037 discloses a method for the preparation of N-nonyl DNJ. In column 4, line 62, U.S. Pat. No. 4,806,650 discloses the preparation of various alkoxy compounds, i.e., with alkyl chains substituted with alkoxy groups. U.S. Pat. No. 4,260,622 discloses the preparation of numerous compounds. Additional references relevant to the preparation of N-substituted-imino-D-glucitol compounds and pro-drugs include U.S. Pat. Nos. 4,182,767 to Murai et al., 4,611,058 to Koebernick, 5,003,072 and 5,411,970 to Partis et al., and 5,151,519 to Behling et al.; PCT International Publication WO 95/19172 to Block et al., and Tan et al. (1991) Journal of Biological Chemistry 266(22): 14504-14510, and the references cited therein.

Methods for introducing oxygen into alkyl side chains are disclosed in U.S. Pat. Nos. 4,260,622 (see col. 42 and col. 60) and 4,639,436 to Junge et al. (see claim 1), 4,806,650 to Schroder et al. and Tan et al., (1994) Glycobiology 4(2):141-149; van den Broek et al. (1994) Recl. Trav. Chim. Pays-Bas 113:107-116 discloses the preparation of ether oxygen-containing DNJ compounds. Non-limiting illustrative preparation procedures are presented below.

In treating hepatitis virus infections, one can use the described N-substitututed-1,5-dideoxy-1,5-imino-D-glucitol compounds alone or in combination in the form of salts derived from inorganic or organic acids. These salts include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate, and undecanoate.

The basic nitrogen-containing groups can be quaternized with agents such as lower alkyl halides, such as methyl, ethyl, propyl, and butyl chloride, bromides, and iodides; dialkyl sulfates such as dimethyl, diethyl, dibuytl, and diamyl sulfates; long chain halides such as decyl, lauryl, myristyl, and stearyl chlorides, bromides, and iodides; aralkyl halides such as benzyl and phenethyl bromides, and others. Water- or oil-soluble or dispersible products are thereby obtained as desired. The salts are formed by combining the basic compounds with the desired acid.

Synthesis routes of preferred compounds will now be described.

Preparation of N-Oxaalkyldeoxynorjirimycin

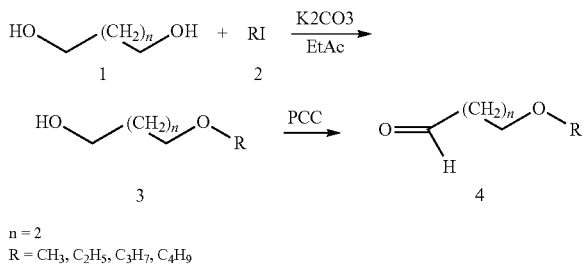

n = 2
R = $CH_3$, $C_2H_5$, $C_3H_7$, $C_4H_9$ romethane (35 ml for 2 gms 3) was stirred at room temperature for 4 hrs. The reaction mixture was passed through column (SiO2, 200-400 mesh, 60 A°) and eluted with dichloromethane to give aldehyde (4) in 90% yield.

N-Oxaalkyldeoxynorjirimycin (6): A mixture of deoxynorjirimycin (5, 1.0 equiv.), aldehyde (4, 2 equiv.) and molecular sieve (4 A°, 1.2 gm/200 mg DNJ) in ethanol (200 proof, 70 ml) was stirred under nitrogen at room temperature for 40 hrs until Scheiff base formation is complete. Pd—C (5%) was added the reaction mixture and then hydrogenated in presence of acetic acid (cat. amt.) under 50 psi at room temperature for 24 hrs. Reaction mixture was filtered and the solvent was removed under vacuum to afford (6) as sticky product. Trituration of the crude product (6) in t-butyl methyl ether gave crystalline product (6).

6, n=2, R=CH3
MP; 86-88° C.
6, n=2, R=C2H5
MP; 99-100° C.
6, n=2, R=C3H7
MP; 88-90° C.
6, n=3, R=C2H5
MP; 88-90° C.
6, n=2, R=C3H7
MP; 120-121° C.
6, n=2, R=C4H9
MP; 114-116° C.

Preparation of N-alkyl, N-alkenyl and N-hydroxylalkyl-deoxynorjirimycin n-Butylcyclohexane series General Procedure:

O-Alkylglycol (3): A mixture of diol (1, 1.9 equiv.), anhydrous potassium carbonate (3.6 equiv.) and alkyl iodide (1 equiv.) in dry ethylacetate (50 ml for 3 gm diol) was refluxed under nitrogen for 40 hrs. Solids were filtered off and the filtrate was washed with water until diol was not detected by TLC in the organic layer. Organic layer was washed by brine and dried over sodium sulfate. The mixture was filtered and the filtrate was concentrated under vacuum to give a colorless oil (90%). The product (3) was used without any purification in the next step.

Oxidation of O-alkylglycol (4): A solution of 3 (1 equiv.) and pyridinium chlrochromate (1.2 equiv.) in dichlo-

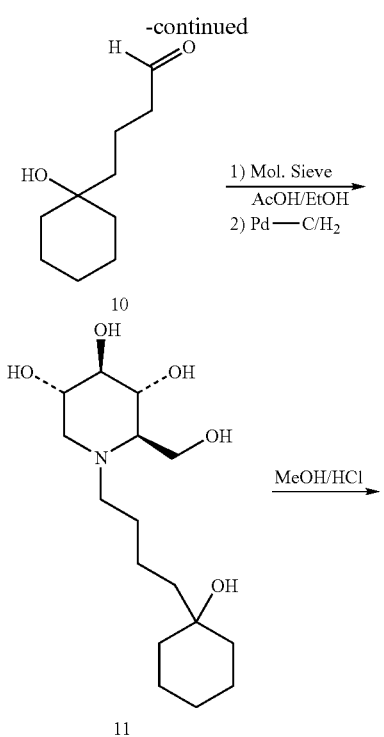

the mixture was stirred at ambient temperature for 3 hours. The reaction mixture was passed through a silica column and eluted by methylene chloride to afford a pure hydroxy-aldehyde, 9 (0.7 gms).

1-n-Butyl-4-N-deoxynorjirimycin-1-cyclohexanol (11)

A suspension of deoxynoijirimycin (DNJ) (255 mg, 1.56 mmol), hydroxyaldehyde (9, 400 mg, 2.35 mmol) and molecular sieves (4 A°, 2.0 gms) in ethanol (200 proof, 25 ml) and catalytic amount of glacial acetic acid was stirred under nitrogen atmosphere for 24 hours at ambient temperature. The reaction mixture was then hydrogenated at 55 psi for 24 hours in presence of 5% Pd on carbon (20 mg). The catalyst was filtered off and the solvent was removed under vacuum to provide 11 (200 mg) after trituration in MTBE.

1-n-Butyl-4-N-deoxynorjirimycin-1-cyclohexene (12)

A solution of 11 (50 mg) in methanolic-HCl was stirred at rt for 17 hrs under N2 atmosphere. The solvent was distilled out under vacuum and the resulting viscous liquid was triturated in methyl-t-butylether to afford crystalline product, 12 (39 mg)

n-Pentylcyclohexane Series

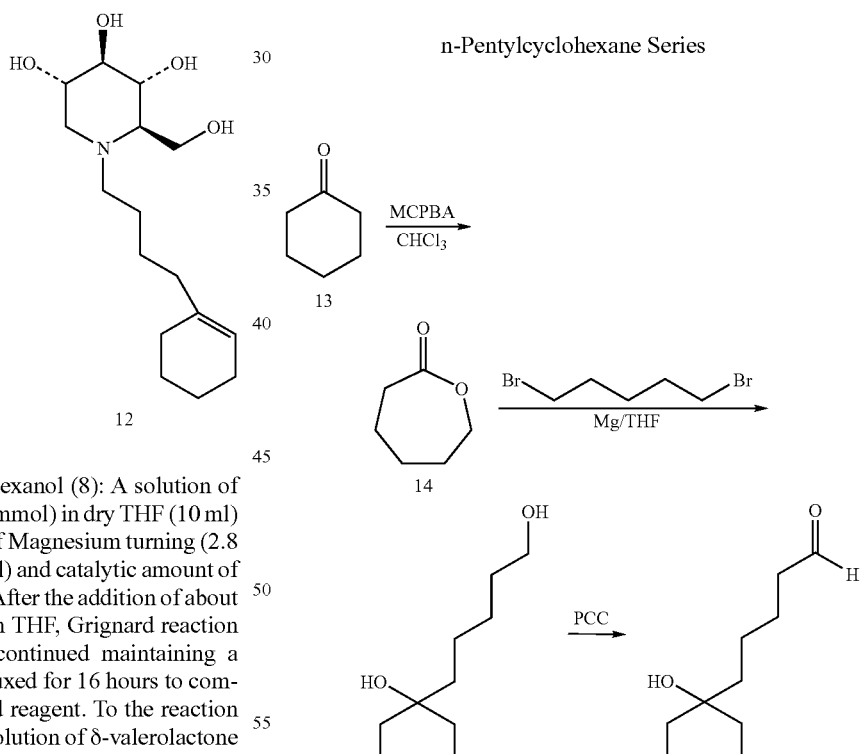

1-(4'-Hydroxy-n-butyl)-1-cyclohexanol (8): A solution of 1,5-dibromopentane (5 gms, 23.15 mmol) in dry THF (10 ml) was added slowly to a suspension of Magnesium turning (2.8 gms, 112 mmole) in dry THF (50 ml) and catalytic amount of iodine under nitrogen atmosphere. After the addition of about 3 ml of dibromopentane solution in THF, Grignard reaction was initiated. The addition was continued maintaining a gentle reflux. The mixture was refluxed for 16 hours to complete the formation of the Grignard reagent. To the reaction mixture was added a solution of a solution of δ-valerolactone (2.13 gms, 21.3 mmol) in dry THF (50 ml). The resulting mixture was refluxed for 6 hours under nitrogen and then quenched by addition of saturated solution of ammonium chloride at 0° C. The product was extracted in ethylacetate. Organic layer was washed with water, brine and dried over anh. Na2SO4. Drying agent was filtered off and the solvent was removed under vacuum to give 2.7 gms of diol (8), which was used without any further purification in the next step.

1-(4'-formyl-n-butyl)-1-cyclohexanol (9): To a solution of 8 (10 gm, 6.33 mmol) in methylene chloride (25 ml) was added pyridinium chlorochromate (1.64 gm, 7.6 mmol) and

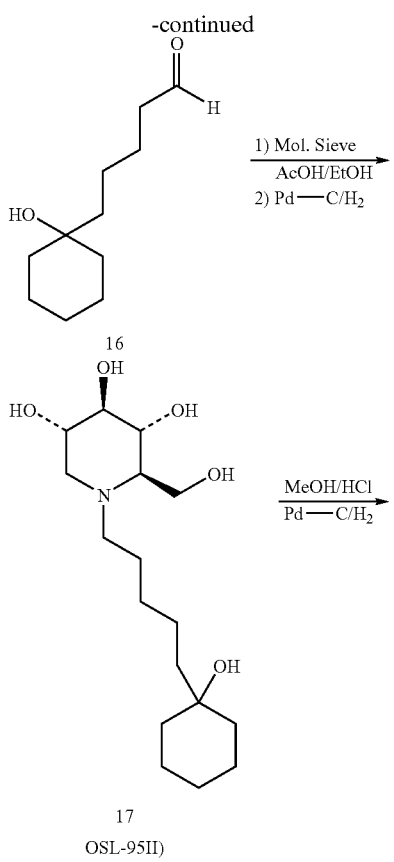

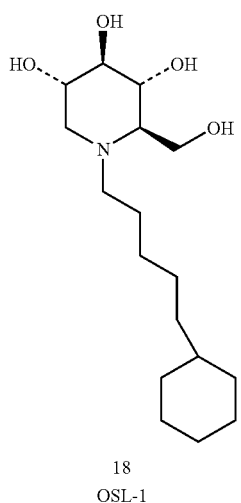

the addition of about 5 ml of dibromopentane solution in THF, Grignard reaction was initiated. The addition was continued maintaining a gentle reflux. The mixture was refluxed for 16 hours to complete the formation of the Grignard reagent. To the reaction mixture was added a solution of a solution of lactone (5 gms, 43.8 mmol) in dry THF (30 ml). The resulting mixture was refluxed for 6 hours under nitrogen and then quenched by addition of saturated solution of ammonium chloride at 0° C. The product was extracted in ethylacetate. Organic layer was washed with water, brine and dried over anh. Na2SO4. Drying agent was filtered off and the solvent was removed under vacuum to give 6.0 gms of diol (15), which was used without any further purification in the next step.

1-(4'-formyl-n-pentyl)-1-cyclohexanol (16): To a solution of 15 (2.5 gm, 13.44 mmol) in methylene chloride (30 ml) was added pyridinium chlorochromate (3.5 gm, 16.33 mmol) and the mixture was stirred at ambient temperature for 17 hours. The reaction mixture was passed through a silica column and eluted by methylene chloride to afford a pure hydroxy-aldehyde, 16 (1.7 gms).

1-n-pentyl-4-N-deoxynorjirimycin-1-cyclohexanol (17)

A suspension of deoxynoijirimycin (5) (DNJ) (100 mg, 0.63 mmol), hydroxyaldehyde (16, 150 mg, 0.81 mmol) and molecular sieves (4AO, 2.0 gms) in ethanol (200 proof, 25 ml) and catalytic amount of glacial acetic acid was stirred under nitrogen atmosphere for 24 hours at ambient temperature. The reaction mixture was then hydrogenated at 55 psi for 24 hours in presence of 5% Pd on carbon (20 mg). The catalyst was filtered off and the solvent was removed under vacuum to provide 11 (83 mg) after trituration in MTBE.

1-n-Butyl-4-N-deoxynorjirimycin-1-cyclohexene (18)

A solution of 17 (40 mg) in methanolic-HCl was stirred at rt for 17 hrs under N2 atmosphere and then transferred to a parr bottle containing 5% Pd—C (10 mg). The mixture was hydrogenated at rt and 55 psi for 24 hrs. The catalyst was filtered off and the solvent was removed to give a viscous liquid which on trituration in methylt-butylether gave a crystalline product, 18 (30 mg).

n-Hexylcyclohexane Series

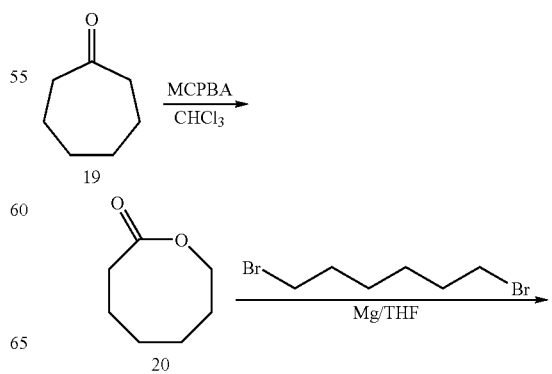

Cyclohexyllactone (14): A solution of cyclohexanone (10 gms, 102 mmol) in chloroform (50 ml) was added to a solution of m-chloroperbenzoic acid (26.4 gms, 153 mmol) in chloroform (132 ml) and stirred at rt for 20 hrs. The reaction mixture was washed by aq Na2CO3 solution (5%, 3×50 ml) until pH aq layer was at 8-9. Organic layer was washed with water and brine and dried over Na2SO4. The insolubles wer filtered off and the organic layer was concentrated under vacuum to give the lactone (14) (9.9 gms)

1-(4'-Hydroxy-n-pentyl)-1-cyclohexanol (15): A solution of 1,5-dibromopentane (11.1 gms, 48.24 mmol) in dry THF (30 ml) was added slowly to a suspension of Magnesium turning (3.2 gms, 131 mmole) in dry THF (100 ml) and catalytic amount of iodine under nitrogen atmosphere. After 23
-continued

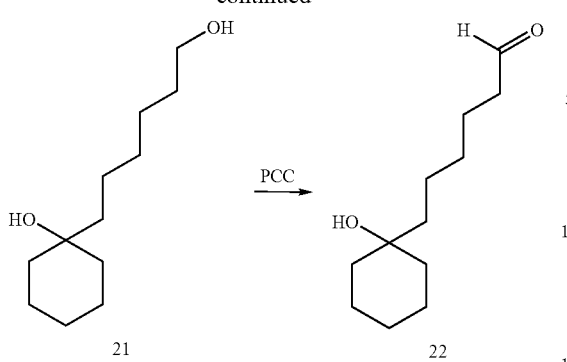

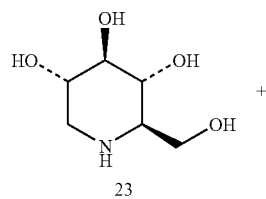

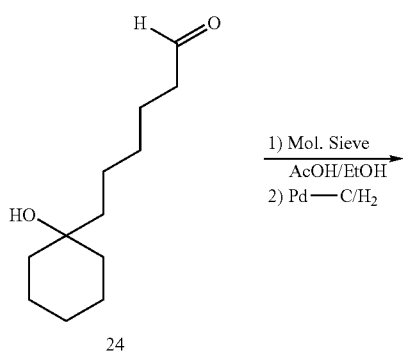

24
-continued

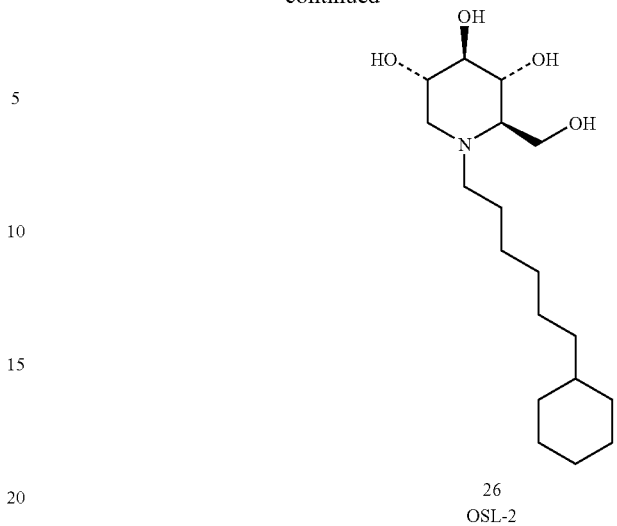

Cycloheptylactone (20): A solution of cycloheptanone (5 gms, 44 mmol) in chloroform (100 ml) was added to a solution of m-chloroperbenzoic acid (12.3 gms, 79.3 mmol) in chloroform (75 ml) and stirred at rt for 36 hrs. The reaction mixture was filtered and the filtrate washed with aq Na2CO3 solution (5%, 3×50 ml) until pH aq layer was at 8-9. Organic layer was washed with water and brine and dried over Na2SO4. The insolubles wer filtered off and the organic layer was concentrated under vacuum to give the lactone (20) (3.5 gms) as waxy solid.

1-(4'-Hydroxy-n-hexyl)-1-cyclohexanol (21): A solution of 1,5-dibromopentane (5.66 gms, 24.6 mmol) in dry THF (30 ml) was added slowly to a suspension of Magnesium turning (3.2 gms, 131 mmole) in dry THF (70 ml) and catalytic amount of iodine under nitrogen atmosphere. After the addition of about 5 ml of dibromopentane solution in THF, Grignard reaction was initiated. The addition was continued maintaining a gentle reflux. The mixture was refluxed for 18 hours to complete the formation of the Grignard reagent. To the reaction mixture was added a solution of a solution of lactone (20, 3 gms, 23.4 mmol) in dry THF (20 ml). The resulting mixture was refluxed for 10 hours under nitrogen and then quenched by addition of saturated solution of ammonium chloride at 0° C. The product was extracted in ethylacetate. Organic layer was washed with water, brine and dried over anh. Na2SO4. Drying agent was filtered off and the solvent was removed under vacuum to give 2.8 gms of diol (21), which was used without any further purification in the next step.

1-(4'-Formyl-n-hexyl)-1-cyclohexanol (22): To a solution of 21 (2.8 gm, 14.0 mmol) in methylene chloride (15 ml) was added pyridinium chlorochromate (3.5 gm, 16.33 mmol) and the mixture was stirred at ambient temperature for 18 hours. The reaction mixture was passed through a silica column and eluted by methylene chloride to afford a pure hydroxy-aldehyde, 16 (1.1 gms).

1-n-Hexyl-4-N-deoxynorjirimycin-1-cyclohexanol (25)

A suspension of deoxynorjirimycin (5) (DNJ) (100 mg, 0.63 mmol), hydroxyaldehyde (22, 300 mg, 1.5 mmol) and molecular sieves (4A°, 2.0 gms) in ethanol (200 proof, 25 ml) and catalytic amount of glacial acetic acid was stirred under

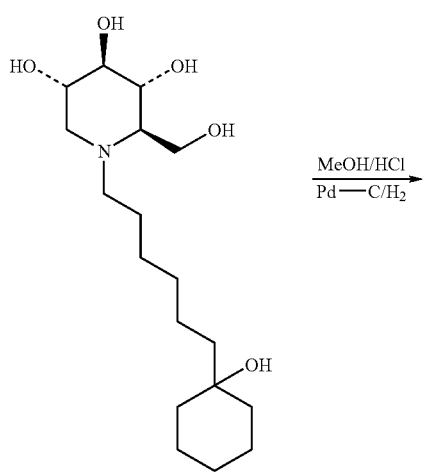

nitrogen atmosphere for 24 hours at ambient temperature. The reaction mixture was then hydrogenated at 55 psi for 24 hours in presence of 5% Pd on carbon (20 mg). The catalyst was filtered off and the solvent was removed under vacuum to provide 25 (125 mg) after trituration in MTBE.

1-n-lHexyl-4-N-deoxynorj irimycin-1-cyclohexene (26)

A solution of 17 (70 mg) in methanolic-HCl was stirred at RT for 15 hrs under nitrogen atmosphere and then transferred to a parr bottle containing 5% Pd—C (25 mg). The mixture was hydrogenated at rt and 55 psi for 17 hrs. The catalyst was filtered off and the solvent was removed to give a viscous liquid which on trituration in dry acetone gave a crystalline product, 18 (47 mg).

A person skilled in the art would appreciate that obtaining other N-substituents in accordance with formula 1 is within available techniques and guidance provided in references listed in this disclosure.

The embodiments disclosed can be administered in a form of pharmaceutically acceptable salts or prodrugs.

Also included are the tautomers of the substituents on the various disclosed compounds. Non-limiting examples of tautomers are ketone/enol tautomers, imino/amino tautomers, N-substituted imino/N-substituted amino tautomers, thiol/thiocarbonyl tautomers, and ring-chain tautomers such as the five and six membered ring oxygen, nitrogen, sulfur, or oxygen- and sulfur-containing heterocycles also containing substituents alpha to the heteroatoms. Also specifically included are enantiomers and diastereomers, as well as racemates and isomeric mixtures of the compounds discussed herein.

Embodients can include nucleoside and nucleotide compounds, such as those disclosed in U.S. Pat. No. 6,809,083.

N-substituted-1,5-dideoxy-1,5-imino-D-glucitol compounds can be administered to humans in an amount in the range of from about 0.1 mg/kg/day to about 100 mg/kg/day, more preferably from about 1 mg/kg/day to about 75 mg/kg/day, and most preferably from about 5 mg/kg/day to about 50 mg/kg/day.

Nucleoside or nucleotide antiviral compounds, or mixtures thereof, can be administered to humans in an amount in the range of from about 0.1 mg/person/day to about 500 mg/person/day, preferably from about 10 mg/person/day to about 300 mg/person/day, more preferably from about 25 mg/person/cay to about 200 mg/person/day, even more preferably from about 50 mg/person/day to about 150 mg/person/day, and most preferably in the range of from about 1 mg/person/day to about 50 mg/person/day.

Immunomodulators and immunostimulants can be administered in amounts conventional in the art or lower. For example, thymosin alpha 1 and thymosin fraction 5 are typically administered to humans for the treatment of HBV infections in an amount of about 900 $\mu g/m^2$, two times per week. This dose can be in the range of from about 10 $\mu g/m^2$, two times per week to about 750 $\mu g/m^2$, two times per week, more preferably from about 100 $\mu g/m^2$, two times per week to about 600 $\mu g/m^2$, two times per week, most preferably from about 200 $\mu g/m^2$, two times per week to about 400 $\mu g/m^2$, two times per week. Interferon alpha is typically administered to humans for the treatment of HCV infections in an amount of from about $1\times10^6$ units/person, three times per week to about $10\times10^6$ units/person, three times per week (Simon et al., (1997) Hepatology 25:445-448). This dose can be in the range of from about $0.1\times10^6$ units/person, three times per week to about $7.5\times10^6$ units/person, three times per week, more preferably from about $0.5\times10^6$ units/person, three times per week to about $5\times10^6$ units/person, three times per week, most preferably from about $1\times10^6$ units/person, three times per week to about $3\times10^6$ units/person, three times per week.

Amounts can be determined by routine monitoring of virus in infected patients undergoing therapy. This can be carried out by, for example, monitoring hepatitis viral DNA in patients' serum by slot-blot, dot-blot, or PCR techniques, or by measurement of hepatitis surface or other antigens, such as the e antigen, in serum. Methods therefor are discussed in Hoofnagle et al., (1997) New Engl. Jour. Med. 336(5):347-356, and F. B. Hollinger in Fields Virology, Third Ed., Vol. 2 (1996), Bernard N. Fields et al., Eds., Chapter 86, "Hepatitis B Virus," pp. 2738-2807, Lippincott-Raven, Philadelphia, Pa., and the references cited therein.

Patients can be similarly monitored during combination therapy employing N-substituted-1,5-dideoxy-1,5-imino-D-glucitol compounds and nucleoside and/or nucleotide antiviral agents to determine the lowest effective doses of each.

The doses described above can be administered to a patient in a single dose or in proportionate multiple subdoses. In the latter case, dosage unit compositions can contain such amounts of submultiples thereof to make up the daily dose. Multiple doses per day can also increase the total daily dose should this be desired by the person prescribing the drug.

Aspects of the invention can be formulated as pharmaceutical compositions. Such compositions can be administered orally, parenterally, by inhalation spray, rectally, intradermally, transdermally, or topically in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, for example, Hoover, John E., Remington's Pharmaceutical Sciences, Mack Publishing Co., Easton, Pa. (1975), and Liberman, H. A. and Lachman, L., Eds., Pharmaceutical Dosage Forms, Marcel Decker, New York, N.Y. (1980).

Injectable preparations, for example, sterile injectable aqueous or oleaginous suspensions, can be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and non-ionic detergents, and polyethylene glycols can be used. Mixtures of solvents and wetting agents such as those discussed above are also useful.

Suppositories for rectal administration of the compounds discussed herein can be prepared by mixing the active agent with a suitable non-irritating excipient such as cocoa butter, synthetic mono-, di-, or triglycerides, fatty acids, or polyethylene glycols which are solid at ordinary temperatures but liquid at the rectal temperature, and which will therefore melt in the rectum and release the drug.

Solid dosage forms for oral administration may include capsules, tablets, pills, powders, and granules. In such solid dosage forms, embodiments may be combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, or magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. The compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredient that can be combined with the carrier materials to produce a single dosage form will vary depending upon the patient and the particular mode of administration.

Certain of embodiments include prodrugs. Prodrugs are drugs that can be chemically converted in vivo or in vitro by biological systems into an active derivative or derivatives. Prodrugs are administered in essentially the same fashion as the other aspects of the invention. Non-limiting examples are the esters of the N-substituted-1,5-dideoxy-1,5-imino-D-glucitol compounds of this invention.

Embodiments may be acids or bases. As such, they may be used to form salts with one another. Nucleosides are purine or pyrimidine compounds lacking-a phosphate ester. Nucleosides or nucleotides analogs containing a carboxylic acid moiety could form a salt with an N-substituted-1,5-dideoxy-1,5-imino-D-glucitol compound. Nucleotides are purine or pyrimidine compounds that are mono-, di-, or triphosphate esters. These phosphate esters contain and their free —OH groups that are acidic, and that can form salts with inorganic bases or organic bases. Salt formation with organic bases depends on the pKa of the acid and base. The N-substituted-1,5-dideoxy-1,5-imino-D-glucitol compounds disclosed herein can form pharmaceutically acceptable salts. In the present case, useful salts can be formed not only with pharmaceutically acceptable acids, but also with biologically active acids such as the nucleosides and nucleotides disclosed herein. These salts can be prepared in the conventional manner for preparing salts, as is well known in the art. For example, one can treat the free base of an N-substituted-1,5-dideoxy-1,5-imino-D-glucitol compound with a nucleotide analog to form a salt. This can be performed as a separate chemical reaction, or as part of the formulation process. The limiting reagent in the salt forming reaction is either the acid or base, as selected by the artisan to obtain a suitable biological result. The formulation can contain mixtures of different salts, acids, or free bases as desired. For example, the phosphoric acid form of (−)-2'-deoxy-3'-thiocytidine-5'-triphosphate will form a salt with the base form of N-pentyl(1-hydroxycyclohexyl)-1,5-dideoxy-1,5-imino-D-glucitol, tetrabutyrate. This type of salt can then be provided to the patient in a pharmaceutically acceptable formulation, as a pure single salt, or as part of a mixture. In some cases, the salts can also be used as an aid in the isolation, purification, or resolution of various embodiments.

The regimen for treating a patient suffering from a hepatitis virus infection with the various aspects of the invention is selected in accordance with a variety of factors, including the age, weight, sex, diet, and medical condition of the patient, the severity of the infection, the route of administration, pharmacological considerations such as the activity, efficacy, pharmacokinetic, and toxicology profiles of the particular compounds employed, and whether a drug delivery system is utilized.

Administration of the drug combinations disclosed herein should generally be continued over a period of several weeks to several months or years until virus titers reach acceptable levels, indicating that infection has been controlled or eradicated. As noted above, patients undergoing treatment with the drug combinations disclosed herein can be routinely monitored by measuring hepatitis viral DNA in patients' serum by slot-blot, dot-blot, or PCR techniques, or by measurement of hepatitis antigens, such as hepatitis B surface antigen (HBsAg) and hepatitis B e antigen (HBeAg), in serum to determine the effectiveness of therapy. In chronic hepatitis B, for example, remissions are characterized by the disappearance of hepatitis B viral DNA, i.e., reduction to undetectable levels as measured by hybridization tests capable of detecting levels 24 $10^5$ genomes per ml of serum, and HBeAg from serum despite the continued presence of HBsAg. These serologic events are followed by improvement in the biochemical and histologic features of the disease. The end point of successful treatment in most trials of antiviral therapy is the disappearance of HBeAg and viral DNA from serum. In patients in whom the e antigen disappears, remission is usually sustained, and results in an inactive HBsAg carrier state.

Continuous analysis of the data obtained by these methods permits modification of the treatment regimen during therapy so that optimal amounts of each component in the combination are administered, and so that the duration of treatment can be determined as well. Thus, the treatment regimen/dosing schedule can be rationally modified over the course of therapy so that the lowest amounts of each of the antiviral compounds used in combination which together exhibit satisfactory anti-hepatitis virus effectiveness are administered, and so that administration of such antiviral compounds in combination is continued only so long as is necessary to successfully treat the infection.

Aspects of the invention are illustrated in the examples below, which are not intended to be limiting.

EXAMPLES

Example 1

General Materials and Methods

Cells and viruses. BVDV-free MDBK cells (CCL 22) were obtained from the American Type Culture Collection and propagated in DMEM/F12 essential medium supplemented with penicillin (500 U/ml), streptomycin (500 U/ml), and 10% heat inactivated horse serum (Invitrogen). Cells were maintained in a humidified incubator at 37° C. with 5% CO2. BVDV (NADL strain) was obtained from Dr. Rubin Donis (Univ. of Nebraska-Lincoln). For infections, virus inoculum was added in complete medium and adsorbed for 1 h at 37° C., the inoculum was then removed, the cells washed once with medium and fresh medium containing compounds added. Virus stocks were prepared by freeze-thawing the infected cells and culture supernatant three times followed by centrifugation at 1,000 g for 5 min. Stock titers were determined, and stocks were aliquoted and stored at −80° C. WNV was obtained from a cDNA clone of a human 2002 isolate from Texas (Rossi et al., 2005); virus obtained from BHK cells electroporated with the in vitro synthesized RNA from this cDNA clone was passaged in Vero cells before use in antiviral assays. Dengue virus (DV) serotype 2 was a New Guinea C virus that had been passaged 28 times in suckling mouse brain, twice in Vero cells, and once in C6/36 mosquito cells.

BVDV antiviral and plaque assays. To evaluate antiviral activity against BVDV, a single cycle virus yield reduction assay was performed in the presence of various concentrations of the test compounds. Specifically, $2 \times 10^5$ MDBK cells/well were plated in 24 well plates. Twenty-four hours later, the cells were infected with BVDV at a multiplicity of infection (moi) of 0.5 PFU/cell in 100 ul complete media. After adsorption for 1 h at 37° C., the inoculum was removed, and cells were washed with media before media containing vehicle or various concentrations of each compound was added. At 22 hour post infection, both cell and media were collected and freeze-thawed three times before the virus was titered. For BVDV virus titer determination, $10^{-2}$, $10^{-3}$, and $10^{-4}$ dilutions of virus were inoculated onto MDBK cells as described previously (Gu et al., 2000; Jordan et al., 2002). After absorption and washing the cells were overlaid with medium containing methylcellulose or soft agar and incubated at 37° C. for 3 days or until plaques were visible. Plaques were counted directly under the microscope or after staining with crystal violet in 70% methanol for 15 min.

WNV and DV Yield Reduction assay: Antiviral activity against WNV was evaluated in a yield reduction assay. Briefly, BHK cells were plated in 96-well plates at a concentration of $2.5 \times 10^4$ cells/well. 24 hours after plating, the cells were infected with WNV at an MOI of 0.05. After 1 hour the inoculum was aspirated and the cells re-fed with fresh DMEM containing dilutions of the test compounds. Plates were then incubated at 37° C. for 48 hours, the supernatant collected and the WNV produced titered. For virus titration, Vero cells were plated in 96-well plates at $8.0 \times 10^3$ cells/well and incubated overnight. The Vero cell monolayers were then infected for 1 hour with various dilutions of the WNV supernatant, overlaid with media containing 0.6% tragacanth (ICN, CA) and incubated at 37° C. for 24-30 hours. The culture media was then aspirated; the plate was rinsed, air-dried, and fixed with 50 ul/well acetone/methanol (50:50). Viral foci were detected for enumeration by immunostaining as described previously (Rossi et al., 2005). For antiviral testing against DV, DV serotype 2, drug incubations and titrations were performed essentially as described for WNV, except that the virus was harvested from drug-treated cultures 72 hrs after infection, and foci were stained using hybridoma culture fluid harvested from monoclonal antibody-producing hybridoma clone D1-4G2 (Gentry et al., 1982) following 3 days of incubation on Vero cells under the tragacanth overlay.

HBV antigen assay: Antiviral activity against HBV was determined using HepG2.2.15 cells, which contain a dimer of the HBV genome and express all viral gene products, including envelope glycoproteins (Sells, Chen, and Acs, 1987). Briefly, HepG2.2.15 cells were seeded in 24 well trays, and allowed to grow to confluence prior to addition of drug, as described previously (Simsek et al., 2005). After seven days of treatment, supernatants were harvested and assayed for the presence of the Large Hepatitis B (LHBs) and middle Hepatitis B (MHBs) glycoproteins by electrophoresis through 12% polyacrylamide gels and immunoblotting with a polyclonal antibody that recognizes the pre-S2 region of the LHBs and MHBs proteins (Research Diagnostics Inc., Flanders, N.J.) as described (Simsek et al., 2005). Quantitation was performed using AlphaEase software (Alphalnnotech).

Compound toxicity assay. Compound cytotoxicity was assessed by using an MTT based toxicity assay kit (Sigma, St. Louis, Mo.) as described elsewhere (Gu et al., 2006). Briefly, cells cultured under conditions identical to those used in the viral assay were incubated with various concentrations of the compound for 72 hours. MTT was added to the media to a final concentration of 0.5 mg/ml and was incubated for 3 hours at 37 C. After the culture media was removed, formazan crystals was dissolved by adding 150 ul of solubilization solution (10% Triton X-100, 0.1 N HCl in anhydrous isopropanol) for 15-30 minutes. The absorbance of the dissolved formazan was measured spectrophotometrically at 570 nm with absorbance at 690 nm as background.

Example 2

Oxygenated Alkyl Side Chain Containing DNJ

Figure 1:
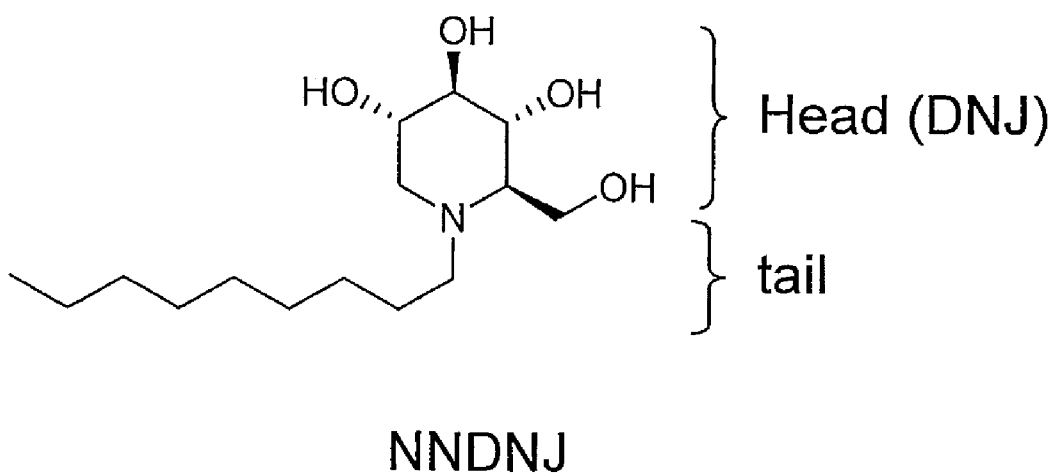
FIG. 1 is a structure of NNDNJ, the prototype iminocyclitol compound consisting of a DNJ head group and an alkyl side chain. NNDNJ alkyl side chain contains 9 carbons.
Figure 2A:
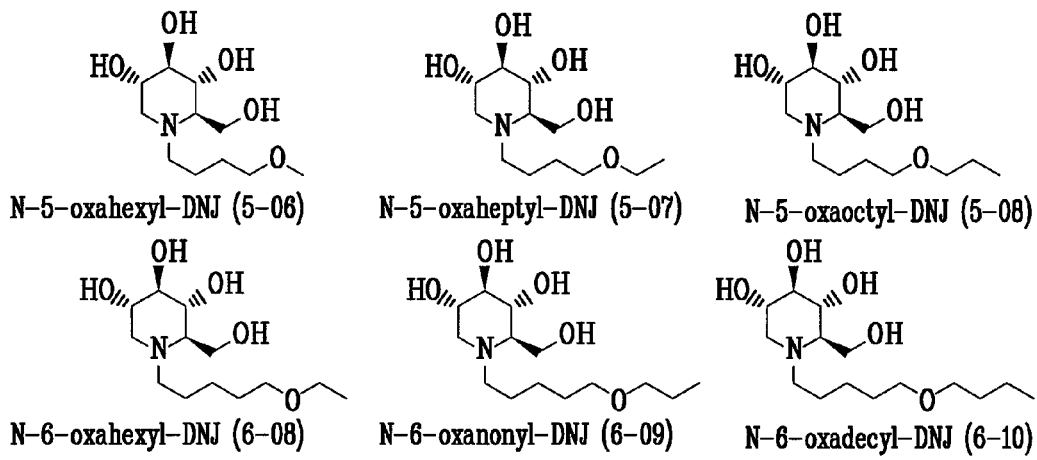
FIG. 2A is a structure of compounds with alkyl side chain of 5 to 9 carbons each is containing an oxygen atom at different positions.

Alkyl side chains of 5, 6, 7, 8 and 9 carbon lengths containing oxygen atom between carbon 4 and 5, and 5 and 6 positions, respectively, were synthesized via reductive amination with RCHO/H2/Pd—C upon DNJ (FIG. 2A).

Figure 2B:
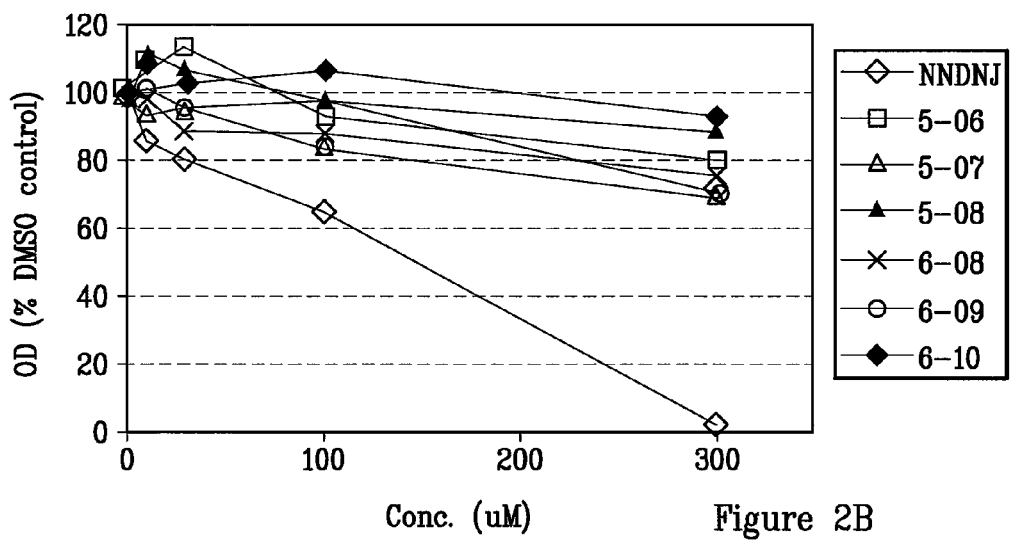
FIG. 2B is a graph demonstrating toxicity profile of the compounds from MTT assay after 72 hours incubation of compound with MDBK cells as described in Materials and Methods. Y axis: MTT OD reading at 570 nm as % of that from cells treated with DMSO control.

The anti-viral activity of this family of compounds against BVDV was then determined by a single cycle viral yield reduction assay in Madin Darby Bovine Kidney (MDBK) cells where the compounds are incubated with cells for 20 hours during the period of infection. Yields of virus were then determined by plaque assay on new MDBK cell monolayers. Compound toxicity was measured by MTT assay and the CC50 determined as the concentration of compound producing 50% reduction in absorption readings. The results show that all N-alkyl DNJs possessing oxygen atoms have significantly less cytotoxicity than NNDNJ with CC50 greater than 300 uM (FIG. 2B). This is consistent with previous findings in which oxygenation and methoxylation of side chains emanating from the ring nitrogen were less toxic in tissue culture and in animals than straight chain alkylated DNJs (Mehta et al., 2002b).

Figure 2C:
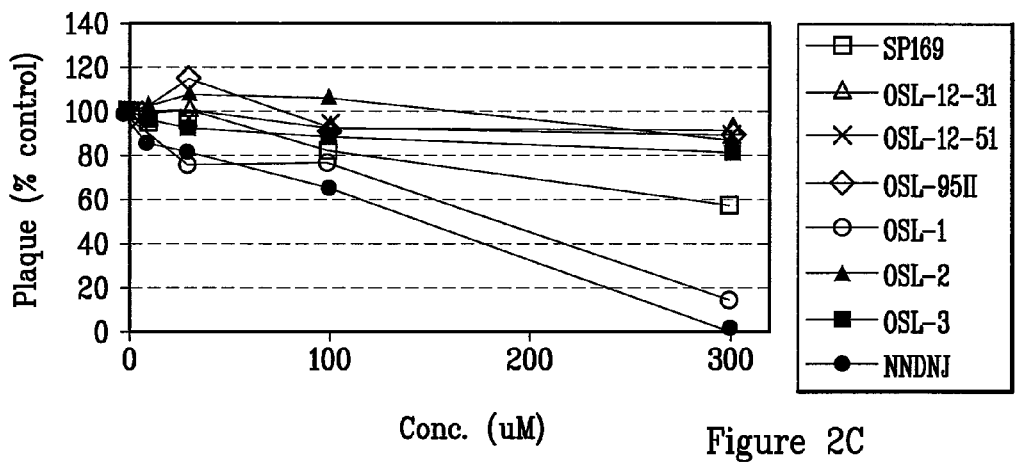
FIG. 2C is a graph demonstrating antiviral activity of 5-06 to 6-10 compounds in a 20 hour BVDV virus yield reduction assay. The data represent the average of duplicate wells in the experiment. X-axis: concentration of compounds in uM; Y-axis: number of plaques as % of control DMSO-treated samples.
Figure 3:
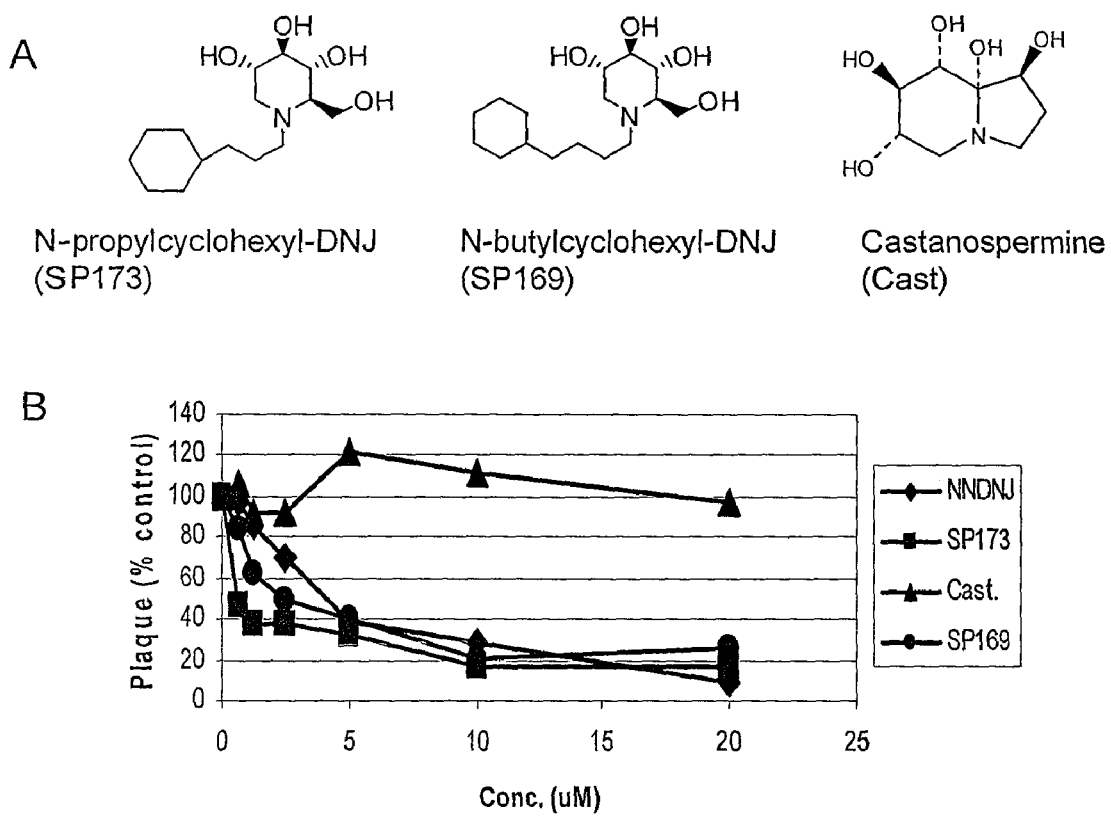
FIG. 3A is a chemical structure of SP169 and a SP173.
FIG. 3B is a graph demonstrating antiviral activity of N-butylcyclohexyl-DNJ (SP169) and N-propylcyclohexyl-DNJ (SP173) against WNV. BHK cells in 96 wells ($2.5 \times 10^4$ cells/well) were infected with WNV at an moi of 0.05 and incubated in the presence of the indicated concentrations of compounds. After 48 hours, the virus released into the media was quantified by plaque assay. The experiments were carried out in duplicates and the average value was plotted. Y axis: number of plaques from drug treated samples as % of DMSO-treated control cells.

Efficacy, however, as determined by the ability to inhibit BVDV yield, was not improved compared to NNDNJ. As shown in FIG. 2C, although the 6'-oxaoctyl-DNJ (6-O8) with the oxygen between the number 5 and 6 carbons retained the best antiviral activity of the series, none of the compounds examined in this series possessed antiviral activity that was equal to or superior to that of NNDNJ.

Example 3

DNJ Containing N-Alkylcycloalkyl Side Chain is Active Against WNV and is Less Toxic Previous work was consistent with the notion that DNJs with alkylcycloalkyl side chains possessed a conformationally restricted element and possessed anti-BVDV activity that is superior to DNJ and NNDNJ (Mehta et al., 2002b). Indeed, as little as 3 μM of compound N-butylcyclohexyl-DNJ (SP169) and N-propylcyclohexyl-DNJ (SP173) inhibited 50% of the yield of BVDV in tissue culture (data not shown). However, the previous studies had been limited to BVDV.

Inventors determined the antiviral activity of the N-butylcyclohexyl-DNJ (SP 169) and N-propylcyclohexyl-DNJ (SP173) against WNV, a member of the flavivirus family that buds from the cell in a manner with similarities to BVDV. For this purpose, BHK cells were infected with WNV at an moi of 0.05, and incubated in either the absence or presence of various concentrations of N-butylcyclohexyl-DNJ (SP169) and N-propylcyclohexyl-DNJ (SP173). After three days, the amount of progeny virus produced was determined by plaque assays on indicator Vero cells. Toxicity was measured in parallel and neither N-butylcyclohexyl-DNJ (SP169) nor N-propylcyclohexyl-DNJ (SP173) had any detectable cell toxicity at 100 uM, the highest concentration tested (data not shown).

FIG. 3B showed that both N-butylcyclohexyl-DNJ (SP169) and N-propylcyclohexyl-DNJ (SP173) inhibited 50% of the WNV progeny produced at concentrations of 5 uM, with N-propylcyclohexyl-DNJ (SP173) consistently outperforming N-butylcyclohexyl-DNJ (SP169) (Table 1). Thus, both compounds were significantly more potent that DNJ, and are comparable to NNDNJ in activity. In this assay, another control compound, Castanospermine was included and it had no significant activity at the highest concentration tested (20 uM), as previously reported (Whitby et al. 2005).

While aspects of the invention has been described in detail and with reference to specific examples thereof, it will be apparent to one skilled in the art that various changes and modifications can be made therein without departing from the spirit and scope thereof.

REFERENCES

An, J., J. Kimura-Kuroda, Y. Hirabayashi, & K. Yasui (1999). Development of a novel mouse model for dengue virus infection. *Virology* 263(1): 70-7.

Bergeron J J, Brenner M B, Thomas D Y, and Williams D B (1994). Calnexin: a membrane-bound chaperone of the endoplasmic reticulum. *Trends Biochem Sci* 19: 124-8.

Block T M, and Jordan R (2001). Iminosugars as possible broad spectrum anti hepatitis virus agents: the glucovirs and alkovirs. *Antivir Chem Chemother* 12: 317-25.

Block T M, Lu X, Platt F M, Foster G R, Gerlich W H, Blumberg B S, and Dwek R A (1994). Secretion of human hepatitis B virus is inhibited by the imino sugar N-butyldeoxynojirimycin. *Proc Natl Acad Sci USA* 91: 2235-9.

Chapel C, Garcia C, Roingeard P, Zitzmann N, Dubuisson J, Dwek R A, Trepo C, Zoulim F, and Durantel D (2006). Antiviral effect of alpha-glucosidase inhibitors on viral morphogenesis and binding properties of hepatitis C virus-like particles. *J Gen Virol* 87: 861-71.

Durantel D, Branza-Nichita N, Carrouee-Durantel S, Butters T D, Dwek R A, and Zitzmann N (2001). Study of the mechanism of antiviral action of iminosugar derivatives against bovine viral diarrhea virus. *J Virol* 75: 8987-98.

Ellgaard L, Molinari M, and Helenius A (1999). Setting the standards: quality control in the secretory pathway. *Science* 286: 1882-8.

Gentry M K, Henchal E A, McCown J M, Brandt W E, and Dalrymple J M (1982). Identification of distinct antigenic determinants on dengue-2 virus using monoclonal antibodies. *Am J Trop Med Hyg* 31: 548-55.

Gu B, Liu C, Lin-Goerke J, Maley D R, Gutshall L L, Feltenberger C A, and Del Vecchio A M (2000). The RNA helicase and nucleotide triphosphatase activities of the bovine viral diarrhea virus NS3 protein are essential for viral replication. *J Virol* 74: 1794-800.

Gu B, Ouzunov S, Wang L, Mason P, Bourne N, Cuconati A, and Block T M (2006). Discovery of small molecule inhibitors of West Nile virus using a high-throughput sub-genomic replicon screen. *Antiviral Res* 70:39-50.

Gubler, D. J. 1998. Dengue and dengue hemorrhagic fever. Clin. Microb. Revs. 11: 480-496.

Guo, J. T., J. Hayashi and C. Seeger. 2005. West Nile Virus inhibits the signal transduction pathway of alpha interferon. J. Virology 79: 1343-50.

Helenius A, and Aebi M (2004). Roles of N-linked glycans in the endoplasmic reticulum. *Annu Rev Biochem* 73: 1019-49.

Jordan R, Nikolaeva O V, Wang L, Conyers B, Mehta A, Dwek R A, and Block T M (2002). Inhibition of host E R glucosidase activity prevents Golgi processing of virion-associated bovine viral diarrhea virus E2 glycoproteins and reduces infectivity of secreted virions. *Virology* 295: 10-9.

Mackenzie J M, and Westaway E G (2001). Assembly and maturation of the flavivirus Kunjin virus appear to occur in the rough endoplasmic reticulum and along the secretory pathway, respectively. *J Virol* 75: 10787-99.

Mehta A, Carrouee S, Conyers B, Jordan R, Butters T, Dwek R A, and Block T M (2001). Inhibition of hepatitis B virus DNA replication by imino sugars without the inhibition of the DNA polymerase: therapeutic implications. *Hepatology* 33: 1488-95.

Mehta A, Conyers B, Tyrrell D L, Walters K A, Tipples G A, Dwek R A, and Block T M (2002a). Structure-activity relationship of a new class of anti-hepatitis B virus agents. *Antimicrob Agents Chemother* 46: 4004-8.

Mehta A, Lu X, Block T M, Blumberg B S, and Dwek R A (1997). Hepatitis B virus (HBV) envelope glycoproteins vary drastically in their sensitivity to glycan processing: evidence that alteration of a single N-linked glycosylation site can regulate HBV secretion. *Proc Natl AcadSci USA* 94: 1822-7.

Mehta A, Ouzounov S, Jordan R, Simsek E, Lu X, Moriarty R M, Jacob G, Dwek R A, and Block T M (2002b). Imino sugars that are less toxic but more potent as antivirals, in vitro, compared with N-n-nonyl DNJ. *Antivir Chem Chemother* 13: 299-304.

Mehta A S, Gu B, Conyers B, Ouzounov S, Wang L, Moriarty R M, Dwek R A, and Block T M (2004). alpha-Galactosylceramide and novel synthetic glycolipids directly induce the innate host defense pathway and have direct activity against hepatitis B and C viruses. *Antimicrob Agents Chemother* 48:2085-90.

Monath T, J. Liu, N. Kanesa-Thasan, Gwendolyn Myers et al 2006. A Live attenuated recombinant West Nile Virus Vaccine. Proc. Natl. Acad. Sci. USA. 103: 6694-6699

Norton P A, Conyers B, Gong Q, Steel L F, Block T M, and Mehta A S (2005). Assays for glucosidase inhibitors with potential antiviral activities: secreted alkaline phosphatase as a surrogate marker. *J Virol Methods* 124:167-72.

Ou W J, Cameron P H, Thomas D Y, and Bergeron J J (1993). Association of folding intermediates of glycoproteins with calnexin during protein maturation. *Nature* 364:771-6.

Ouzounov S, Mehta A, Dwek R A, Block T M, and Jordan R (2002). The combination of interferon alpha-2b and n-butyl deoxynojirimycin has a greater than additive antiviral effect upon production of infectious bovine viral diarrhea virus (BVDV) in vitro: implications for hepatitis C virus (HCV) therapy. *Antiviral Res:* 425-35.

Rossi S L, Zhao Q, O'Donnell V K, and Mason P W (2005). Adaptation of West Nile virus replicons to cells in culture and use of replicon-bearing cells to probe antiviral action. *Virology* 331:457-70.

Sells M A, Chen M L, and Acs G (1987). Production of hepatitis B virus particles in Hep G2 cells transfected with cloned hepatitis B virus DNA. *Proc Natl Acad Sci USA* 84:1005-9.

Simsek E, Mehta A, Zhou T, Dwek R A, and Block T M (2005). Hepatitis B virus large and middle glycoproteins are degraded by a proteasome pathway in glucosidase-inhibited cells but not in cells with functional glucosidase enzyme. *J Virol* 79: 12914-20.

Solomon, T, R Kneen, N M Dung et al 1998. Poliomyeltis like illness due to Japanese encephalitis virus. Lancet 351: 1094-1097.

Tan A, van den Broek L, Bolscher J, Vermaas D J, Pastoors L, van Boeckel C, and Ploegh H (1994). Introduction of oxygen into the alkyl chain of N-decyl-dNM decreases lipophilicity and results in increased retention of glucose residues on N-linked oligosaccharides. *Glycobiology* 4:141-9.

Tan A, van den Broek L, van Boeckel S, Ploegh H, and Bolscher J (1991). Chemical modification of the glucosidase inhibitor 1-deoxynojirimycin. Structure-activity relationships. *J Biol Chem* 266:14504-10.

Tomori O 1999 Impact of yellow fever virus on the developing world. Adv. Virus Res. 53: 5-34.

Wu S F, Lee C J, Liao C L, Dwek R A, Zitzmann N, and Lin Y L (2002). Antiviral effects of an iminosugar derivative on flavivirus infections. *J Virol* 76:3596-604.

Zitzmann N, Mehta A S, Carrouee S, Butters T D, Platt F M, McCauley J, Blumberg B. S., Dwek R A, and Block T M (1999). Imino sugars inhibit the formation and secretion of bovine viral diarrhea virus, a pestivirus model of hepatitis C virus: implications for the development of broad spectrum anti-hepatitis virus agents. *Proc Natl Acad Sci USA* 96:11878-82.

What is claimed:

1. A 1,5-dideoxy-1,5-imino-D-glucitol derivative compound having the general formula (I)

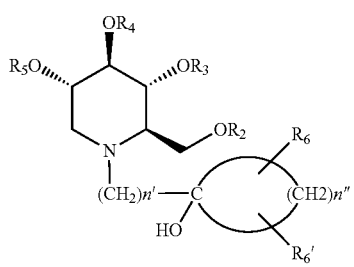

wherein $R^2$, $R^3$, $R^4$ and $R^5$ are the same or different and are selected from the group consisting of hydrogen, acyl, benzyl, alkyl, aryl, sulfonyl, phosphonyl, silyl, $R_6$ is at least one of alkyl or branched alkyl, heteroalkyl, hydrogen, or aryl, $R_6'$ is hydrogen, n'=2-10, n"=4-6 or an enantiomers or stereoisomer of said compound and physiologically acceptable salts of said compound, enantiomer or stereoisomer.

2. The compound of claim 1, wherein n' is 4, 5, or 6.

3. The compound of claim 1, wherein the 1,5-dideoxy-1,5-imino-D-glucitol derivative compound is N-pentyl(1-hydroxycyclohexyl)-1,5-dideoxy-1,5-imino-D-glucitol and has the general formula (III):

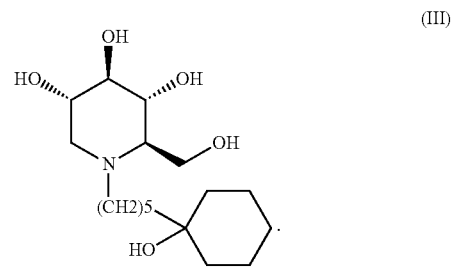

4. The compound of claim 1, wherein the 1,5-dideoxy-1,5-imino-D-glucitol derivative compound is N-butyl(1-hydroxycyclohexyl)-1,5-dideoxy-1,5-imino-D-glucitol and has the general formula (IV):

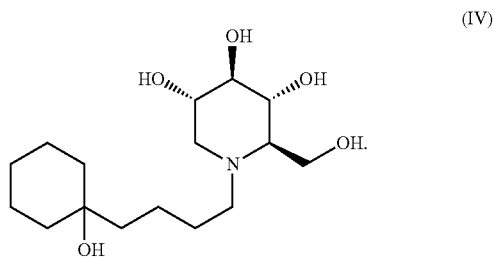

5. The compound of claim 1, wherein the 1,5-dideoxy-1,5-imino-D-glucitol derivative compound is N-hexyl(1-hydroxycyclohexyl)-1,5-dideoxy-1,5-imino-D-glucitol and has the general formula (V):

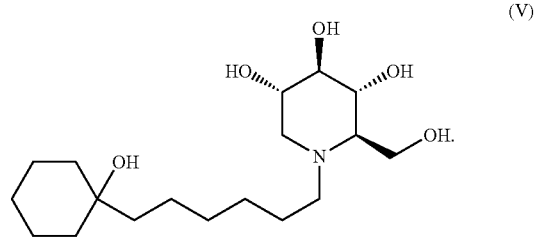

6. An anti-viral composition comprising a 1,5-dideoxy-1,5-imino-D-glucitol derivative compound having the general formula (I)

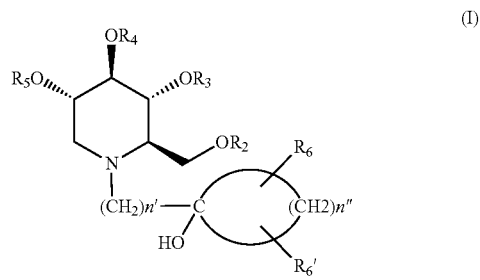

wherein $R^2$, $R^3$, $R^4$ and $R^5$ are the same or different and are selected from the group consisting of hydrogen, acyl, benzyl, alkyl, aryl, sulfonyl, phosphonyl, silyl, $R_6$ is at least one of alkyl or branched alkyl, heteroalkyl, hydrogen, or aryl, $R_6'$ is hydrogen, n'=2-10, n"=4-6, or an enantiomers or stereoisomer of said compound and physiologically acceptable salts of said compound, enantiomer or stereoisomer.

7. The anti-viral compound of claim 6, wherein n' is 4, 5, or 6.

8. A method for inhibiting production of a virus belonging to the Flaviviridae family comprising contacting a mammalian cell infected by said virus with an effective amount of an anti-viral composition comprising the anti-viral compound of claim 6.

9. The method of claim 8, wherein in the 1,5-dideoxy-1,5-imino-D-glucitol derivative compound, $R^7$ is a $C_4$-$C_6$ alkyl moiety.

10. The method of claim 8, wherein the 1,5-dideoxy-1,5-imino-D-glucitol derivative compound is N-pentyl(1-hydroxycyclohexyl)-1,5-dideoxy-1,5-imino-D-glucitol and has the general formula (III):

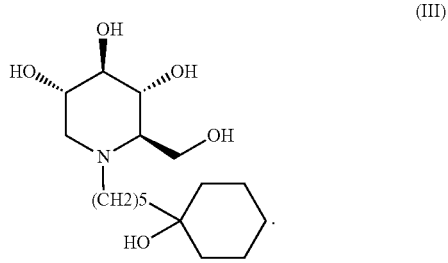

(III)

11. The method of claim 8, wherein the 1,5-dideoxy-1,5-imino-D-glucitol derivative compound is N-butyl(1-hydroxycyclohexyl)-1,5-dideoxy-1,5-imino-D-glucitol and has the general formula (IV):

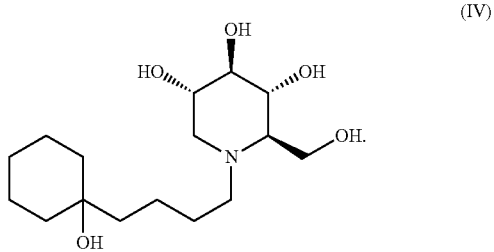

(IV)

12. The method of claim 8, wherein the 1,5-dideoxy-1,5-imino-D-glucitol derivative compound is N-hexyl(1-hydroxycyclohexyl)-1,5-dideoxy-1,5-imino-D-glucitol and has the general formula (V):

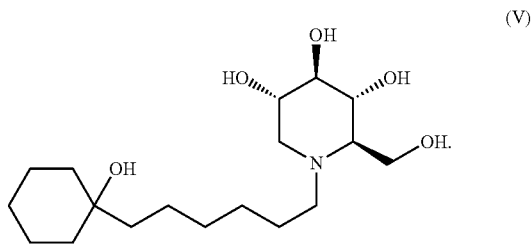

(V)

13. The method of claim 8, wherein the 1,5-dideoxy-1,5-imino-D-glucitol derivative compound, enantiomer, or stereoisomer, or physiologically acceptable salt of said compound, enantiomer, or stereoisomer is administered to a mammal.

14. The method of claim 8, wherein the 1,5-dideoxy-1,5-imino-D-gucitol derivative compound, enantiomer, or stereoisomer, or physiologically acceptable salt of said compound, enantiomer, or stereoisomer is administered to a human.

15. The method of claim 8, wherein the 1,5-dideoxy-1,5-imino-D-glucitol derivative compound, enantiomer, or stereoisomer, or physiologically acceptable salt of said compound, enantiomer, or stereoisomer is administered to said mammalian cell in vivo.

16. The method of claim 8, wherein said virus is at least one of West Nile fever virus, dengue virus, bovine viral diarrhea virus, and hepatitis B virus.

17. The method of claim 11, wherein said virus is a flavivirus.

18. The method of claim 17, wherein the flavivirus is selected from the group consisting of yellow fever virus, Japanese encephalitis virus, Murray Valley encephalitis, Rocio virus, St. Louis encephalitis virus, tick-borne encephalitis virus, Louping ill virus, Powassan virus, Omsk hemorrhagic fever virus and Kyasanur forest disease virus.

19. The method of claim 17, said virus is a pestivirus.

20. The method of claim 17, said virus is at least one of bovine diarrhea virus or hepatitis C virus.

* * * * *

UNITED STATES PATENT AND TRADEMARK OFFICE
CERTIFICATE OF CORRECTION

PATENT NO. : 8,097,728 B2  
APPLICATION NO. : 12/112694  
DATED : January 17, 2012  
INVENTOR(S) : Baohua Gu et al.

Page 1 of 1

It is certified that error appears in the above-identified patent and that said Letters Patent is hereby corrected as shown below:

On the Title Page,
Item (73) Assignees:
Line 2, after "Corporation," insert -- dba Drexel University College of Medicine, --.

On the Title Page,
Item (56), References Cited:
OTHER PUBLICATIONS:
"Dhavale et al.," reference, after "(2003).*" delete "Ramesh" and insert -- Ramesh -- on next line before "et al.,".

In the Specifications:
Column 1,
Line 17, delete "may therefore have certain rights" and insert -- has certain rights --.

Signed and Sealed this
First Day of May, 2012

David J. Kappos
*Director of the United States Patent and Trademark Office*